(12) United States Patent
Yamane et al.

(10) Patent No.: US 6,330,303 B1
(45) Date of Patent: Dec. 11, 2001

(54) X-RAY IMAGING APPARATUS

(75) Inventors: Yasukuni Yamane, Shiki-gun; Shiro Oikawa, Soraku-gun, both of (JP)

(73) Assignees: Sharp Kabushiki Kaisha, Osaka; Shimadzu Corporation, Kyoto, both of (JP)

( * ) Notice: Subject to any disclaimer, the term of this patent is extended or adjusted under 35 U.S.C. 154(b) by 0 days.

(21) Appl. No.: 09/429,012

(22) Filed: Oct. 28, 1999

(30) Foreign Application Priority Data

Nov. 27, 1998 (JP) .................................................. 10-338053

(51) Int. Cl.$^7$ ...................................................... H05G 1/64
(52) U.S. Cl. ...................................... 378/98.8; 250/370.09
(58) Field of Search ........................ 378/98.8; 250/370.09

(56) References Cited

FOREIGN PATENT DOCUMENTS 62-2933   1/1987   (JP) .

OTHER PUBLICATIONS

Zhao et al, "A flat panel detector for digital radiology using active matrix readout of amorphous selenium", *SPIE*, vol. 2708, 1996, pp. 523–532.

Lee et al., "A New Digital Detector for Projection Radiography", *SPIE*, vol. 2432, 1995, pp. 237–249.

*Primary Examiner*—Craig E. Church
(74) *Attorney, Agent, or Firm*—Nixon & Vanderhye, PC

(57) ABSTRACT

A scanning line drive circuit performs not only a sequential scanning function of scanning lines, but also an interlaced scanning function. For instance, in a fluoroscopy mode in which high-speed imaging and real-time imaging are required, the scanning line drive circuit performs interlaced scanning to scan, for example, every other scanning line. With the interlaced scanning, since the scanning lines are scanned one line at a time like the sequential scanning, a variation of charge on a signal line side does not increase during a transition of a scanning line voltage like conventional scanning in which a plurality of scanning lines are scanned simultaneously. It is therefor possible to obtain a good signal-to-noise ratio without an increase in noise due to fluctuations in the scanning line voltage. Moreover, since an increase in the variation of charge in the fluoroscopy mode can be limited by changing a scanning method of the scanning line drive circuit according to an imaging mode, a signal readout circuit does not need to have a complicated structure to limit the increase in the variation of charge.

17 Claims, 18 Drawing Sheets

X-RAY IMAGING APPARATUS

FIELD OF THE INVENTION

The present invention relates to an X-ray imaging apparatus for converting an X-ray image of a specimen into electrical image signals according to the quantity of X-rays passed through the specimen, and more particularly to an X-ray imaging apparatus capable of performing real-time imaging and operating at high speed.

BACKGROUND OF THE INVENTION

Conventionally, in the field of medical diagnosis, an imaging apparatus using a film, an image-intensifier type imaging apparatus, etc. have been used as means for visualizing an X-ray image. In resent years, development of a flat-panel type X-ray imaging apparatus as a new imaging apparatus substituting the above apparatuses is active, and clinical experiments have been partly started.

This flat-panel type X-ray imaging apparatus uses, as a key device, a flat-panel type X-ray detector which is produced by combining a large-area thin-film transistor array technique used in an active matrix type liquid crystal display device and an X-ray conversion film technique for converting X-rays into electrical signals, and has various advantages over conventional X-ray imaging apparatuses. More specifically, the flat-panel type X-ray imaging apparatus achieves an improvement of the image quality and diagnosis support by digital image processing as well as instantaneous conversion of a result of imaging into image signals and display of the result on a display or output of the result to a printer, and easily stores and transfers the result of imaging as digital image information, compared with a conventional film-type imaging apparatus. Moreover, compared with the conventional image-intensifier type imaging apparatus, the flat-panel type X-ray imaging apparatus achieves a significant reduction in its thickness, and provides a large-area, high-resolution X-ray image.

The following description will explain the structure and operational principle of the flat-panel type X-ray imaging apparatus. The specific structure and properties of the flat-panel type X-ray detector are described in detail in documents, for example:

Denny L. Lee, et al., "A new digital detector for projection radiography", SPIE, Vol.2432, pp237–249, 1995; and Wei Zhao, et al., "A flat panel detector for digital radiology using active matrix readout of amorphous selenium", SPIE, vol. 2708, pp523–531, 1996.

FIG. 18 shows an example of a conventional X-ray imaging apparatus using a flat-panel type X-ray detector. The X-ray imaging apparatus includes an X-ray generator 51, a flat-panel type X-ray detector 52, a control device 53, an operator console 54, an image processing device 55, a display device 56, and a printer device 57.

X-rays emitted from the X-ray generator 51 pass through a specimen 58, and are incident on the flat-panel type X-ray detector 52. The incident X-rays are converted into a two-dimensional charge distribution according to the quantity of the incident X-rays, further converted into digital image signals and sequentially output. The digital image signals are subjected to image processing, such as a gray-scale correction, in the image processing device 55, and sent as display signals to the display device 56 where the signals are visualized (displayed). Moreover, the digital image signals are sent to the printer device 57 and output as a print, if necessary. Although not shown in FIG. 18, it is possible to store digital image data in an image storage device or transmit the digital image data to a remote place.

The operator console 54 is provided with a switch for allowing an operator to instruct an irradiation start timing of X-rays, and X-ray imaging is started upon the operation of the switch. Besides, the control device 53 controls the entire sequence and timing.

By the way, the conversion method of the flat-panel type X-ray detector 52 is roughly classified into two types: a direct conversion method of directly converting X-rays into charge by a conversion layer; and an indirect conversion method of converting X-rays into light temporarily using a scintillator and then converting the light signals into electrical signals by a photodiode. The indirect conversion method is disclosed in, for example, Japanese laid-open patent application No. (Tokukaisho) 62-2933 (published Jan. 8, 1987). Here, for the sake of convenience of explanation, the following description will illustrate the direct conversion method.

FIG. 19 shows a schematic structure of essential sections of the flat-panel type X-ray detector 52. A number of pixels 61 are arranged in a matrix form, and each pixel 61 is connected to a scanning line SLj (j=1 to m: m is an integer of not less than 2) and a signal line DLi (i=1 to n: n is an integer of not less than 2) through a TFT 72 (see FIG. 21) as a later-described switching element. Each scanning signal SLj is connected to a scanning line drive circuit 62, while each signal line DLi is connected to a signal readout circuit 63. The scanning line drive circuit 62 and signal readout circuit 63 are controlled by a timing control circuit 64.

As the scanning line drive circuit 62, a gate driver IC (Integrated Circuit) used in a general liquid crystal display device can be used. Besides, as shown in FIG. 20, for example, the signal readout circuit 63 includes: pre-amplifiers 65 which are provided in association with the signal lines DLi, respectively, and perform voltage conversion and amplification of input signals; a multiplexer 66 for switching the outputs from the pre-amplifiers 65 consecutively to an A/D converter 67 in a later stage; and the A/D converter 67 for converting analog image signals from the multiplexer 66 into digital image signals.

FIG. 21 depicts an example of a cross sectional structure of the pixel 61 of the flat-panel type X-ray detector 52 (see FIG. 18). FIG. 22 shows an equivalent circuit of the pixel 61. As illustrated in FIG. 21, the pixel 61 includes a TFT (thin film transistor) 72 formed on a glass substrate 71, a storage capacitor (Cs) 73, etc.

The TFT 72 includes a gate electrode 74 connected to the scanning line SLj, a gate insulating film 75 formed to cover the gate electrode 74, a source electrode 76 and a drain electrode 77 formed on the gate insulating film 75. The source electrode 76 is connected to the signal line DLi, while the drain electrode 77 is connected to a pixel electrode 78.

The storage capacitor 73 is configured such that the pixel electrode 78 and a lower common electrode 80 connected to the negative terminal of a bias power supply 79 face each other with an insulating film 81 therebetween. Additionally, a charge preventing layer 82 is formed to cover the source electrode 76, drain electrode 77 and pixel electrode 78.

As a TFT matrix formed by the TFT 72 and storage capacitor 73, it is possible to use a TFT substrate which is produced in the process of manufacturing an active matrix type liquid crystal display device. For instance, a TFT substrate for use in an amorphous silicone (a-Si) TFT liquid crystal display device has scanning lines, signal lines, storage capacitors, etc., and can be used as the TFT matrix of a flat-panel type X-ray detector 52 by making slight changes.

Further, in each pixel 61, a photoconductive film 83, a dielectric layer 84, and an upper common electrode 85 connected to the positive terminal of the bias power supply 79 are formed successively to cover the TFT 72 and storage capacitor 73, and a pixel capacitor Cp (see FIG. 22) is produced. As a material for the photoconductive film 83, a semiconductor material which absorbs X-rays and converts the X-rays into charge with high efficiency is used. For example, in the above documents, an amorphous selenium (a-Se) film formed in a thickness of 300 to 600 $\mu$m by vacuum evaporation is used.

Next, the following description will explain the operation of the flat-panel type X-ray detector 52 of the above-mentioned structure.

X-rays incident on the photoconductive film 83 are absorbed within the photoconductive film 83, and converted into charge according to the quantity of the X-rays. Since the photoconductive film 83 and storage capacitor 73 structurally form a capacitor which is electrically connected in series, the generated charge (electrons and holes) moves to electrodes of different polarities, respectively, upon application of a bias voltage across the upper common electrode 85 and the lower common electrode 80 by the bias power supply 79, thereby storing predetermined charge in the storage capacitor 73. Hence, the photoconductive film 83 and storage capacitor 73 form an X-ray detecting element which converts X-rays passed through the specimen 58 (see FIG. 18) into charge and stores the charge.

The charge stored in the storage capacitor 73 can be removed from the storage capacitor 73 through the signal line DLi by application of a voltage sufficient for turning on the TFT 72 to the scanning line SLj. Therefore, as illustrated in FIG. 19, by performing line sequential scanning of the scanning lines SLj with the scanning line drive circuit 62, signals over the entire pixels 61 can be obtained. The signals extracted from the pixels 61 are subjected to voltage conversion, amplification, and A/D conversion in the signal readout circuit 63 connected to each column of the signal lines DLi, and the information of the X-ray image is detected as digital image signals.

By the way, the readout operation of the image signals is roughly classified into two categories, according to the objects of flat-panel type X-ray imaging apparatus. One object is to replace an imaging apparatus using an X-ray film with a flat-panel type X-ray imaging apparatus. The other object is to replace an image-intensifier type X-ray imaging apparatus with a flat-panel type x-ray imaging apparatus. Here, the operation associated with the former object is called the "radiography mode", while the operation associated with the latter object is called the "fluoroscopy mode". In other words, a still image of the specimen is obtained in the radiography mode, while a moving image of the specimen is obtained in the fluoroscopy mode.

In the radiography mode, a resolution as high as or higher than the current X-ray film, low noise, and a wide dynamic range are required. In this mode, a relatively large quantity of X-rays of several mR per frame may be irradiated, and a readout time of up to several seconds is also allowed. Thus, this mode can be relatively easily achieved.

On the other hand, in the fluoroscopy mode, a high-speed imaging of around 30 frames per second is required, and it is, for example, necessary to image a movement of the heart of an infant and a movement of a taken contrast medium in the esophagus in real time. In this mode, considering the exposure of X-rays, the quantity of X-rays which can be irradiated on the specimen is as small as several tens $\mu$R or less per frame. Therefore, in the fluoroscopy mode, it is necessary to perform imaging with extremely high sensitivity and low noise. It is thus difficult to achieve the fluoroscopy mode compared with the radiography mode.

As measures to easily achieve the fluoroscopy mode, development of a photoconductive film with a high X-ray conversion efficiency and an attempt to improve the X-ray conversion efficiency by increasing the thickness of the photoconductive film have been carried out from the aspect of the device.

On the other hand, from the aspect of the drive circuit, a proposal to perform high-speed scanning by driving a plurality of scanning lines simultaneously to increase the quantity of signals instead of sacrificing the resolution has been made. When simultaneous driving of a plurality of scanning lines is performed, since the signals from a plurality of pixels are extracted to the respective signal lines, the quantity of signals is increased compared with driving of a single scanning line. For example, if the amount of charge stored in the storage capacitor of each of the pixels is uniform, when two scanning lines are driven simultaneously, the quantity of signals extracted to the signal lines is two times that extracted by driving a single scanning line. Similarly, when three scanning lines are driven simultaneously, three times the quantity of signals extracted by driving a single scanning line is extracted to the signal lines.

By the way, in practice, there is a problem in driving a plurality of scanning lines simultaneously. Specifically, since a parasitic capacitance exists between the scanning line and signal line, a significant amount of charge moves to the signal line through the parasitic capacitance upon a transition of the voltage of the scanning line, and this effect becomes stronger with an increase in the number of scanning lines which are scanned simultaneously.

The degree of the effect can be estimated as follows. As the parasitic capacitance between the scanning line and signal line, there are mainly the parasitic capacitance at a crossed lines section, parasitic capacitance between the gate and source and between the gate and drain. These parasitic capacitances usually amount to a total of around 0.02 to 0.06 pF. Besides, as the drive voltage of the scanning line, an amplitude of around 15 to 25 V is generally selected to sufficiently turn on/off the TFT. Therefore, a variation of the charge on the signal line side due to the transition of the voltage of a single scanning line is around 0.3 to 1.5 pC. This variation of charge is two-digit scale larger than a maximum signal charge (utmost several fC to tens of several fC) expected for each pixel in the fluoroscopy mode.

In the case of a TFT array having 2000 or more pixels per side of an around 40 cm square screen, when a general process is used, the resistance of the overall length of the scanning lines is around 10 k$\Omega$ and the capacitance is around 100 pF. Therefore, the drive waveform on the scanning line varies according to the distance from the scanning line drive circuit, and a transient response of the variation of charge on the signal line side during the transition of voltage of the scanning line also varies according to the distance between the scanning line drive circuit and each signal line. Hence, when the variation of charge on the signal line side due to the transition of the scanning line drive voltage is increased, since the non-uniformity in a scanning line direction is increased, it is necessary to take a countermeasure against the non-uniformity in a scanning line direction.

As described above, simultaneous driving of a plurality of scanning lines increases the variation of the voltage associated with the driving. As a countermeasure, it is necessary to perform a special offset adjustment and delay the time of signal sampling in the signal readout circuit. As a result, the circuit becomes complicated, and noise due to fluctuations in the scanning line voltage is increased.

SUMMARY OF THE INVENTION

It is an object of the present invention to provide an X-ray imaging apparatus capable of providing a good signal-to-noise ratio as well as limiting an increase in the variation of charge on the signal line side during a transition of voltage of a scanning line, without causing a signal readout circuit to have a complicated structure.

In order to achieve the above object, an X-ray imaging apparatus of the present invention includes: X-ray irradiating means for irradiating X-rays on a specimen; X-r ay detect ing elements, arranged two-dimensionally, for converting X-rays obtained through the specimen into charge and storing the charge; switching elements provided in association with the X-ray detecting elements, respectively; and a scanning line drive circuit for driving the switching elements row by row through scanning lines, and is characterized in that the scanning line drive circuit drives the switching elements by selectively performing sequential scanning of the scanning lines or interlaced scanning which scans at least every other scanning line, according to an imaging mode of the specimen.

With this structure, when X-rays are irradiated on the specimen by the X-ray irradiating means, the X-rays reach the two-dimension ally arranged X-ray detecting elements through the specimen, and are converted into charge by the X-ray detecting elements. When the scanning line drive circuit drives the switching elements associated with the X-ray detecting elements through the scanning lines, signals according to the charge can be obtained row by row.

Examples of the above-mentioned imaging mode include a radiography mode for imaging a static specimen and a fluoroscopy mode for imaging a dynamic specimen. Here, the scanning line drive circuit selectively performs sequential scanning of the scanning lines or interlaced scanning which scans at least every other scanning line, according to an imaging mode of the specimen, to drive the switching elements. Therefore, for example, the switching elements can be driven by the sequential scanning of the scanning lines in the radiography mode, and the switching elements can be driven by the interlaced scanning of the scanning lines in the fluoroscopy mode in which high-speed imaging or real-time imaging are required.

With a prior art, in the fluoroscopy mode, since the switching elements are driven by simultaneous scanning of a plurality of scanning lines, the variation of charge on the signal line side during a transition of the scanning line voltage increases depending on the number of scanning lines scanned simultaneously. However, with the use of the above-mentioned interlaced scanning, since the scanning lines is scanned one line at a time, the variation of charge is the same as that in the sequential scanning, and does not increase like the prior art.

Hence, the increase in the variation of charge during a transition of the scanning line voltage leads to an increase of noise due to fluctuations in the scanning line voltage. However, with the above-mentioned structure, since the increase in the variation of charge can be limited, it is also possible to limit such an increase in noise. In other words, it is possible to provide a good signal-to-noise ratio by limiting the increase in the variation of charge on the signal line side during a transition of the scanning line voltage, without causing the signal readout circuit to have a complicated structure.

For a fuller understanding of the nature and advantages of the invention, reference should be made to the ensuing detailed description taken in conjunction with the accompanying drawings.

DESCRIPTION OF THE PREFERRED EMBODIMENTS

[First Embodiment]

The following description will explain an embodiment of the present invention with reference to FIGS. 1 to 13.

Figure 2:
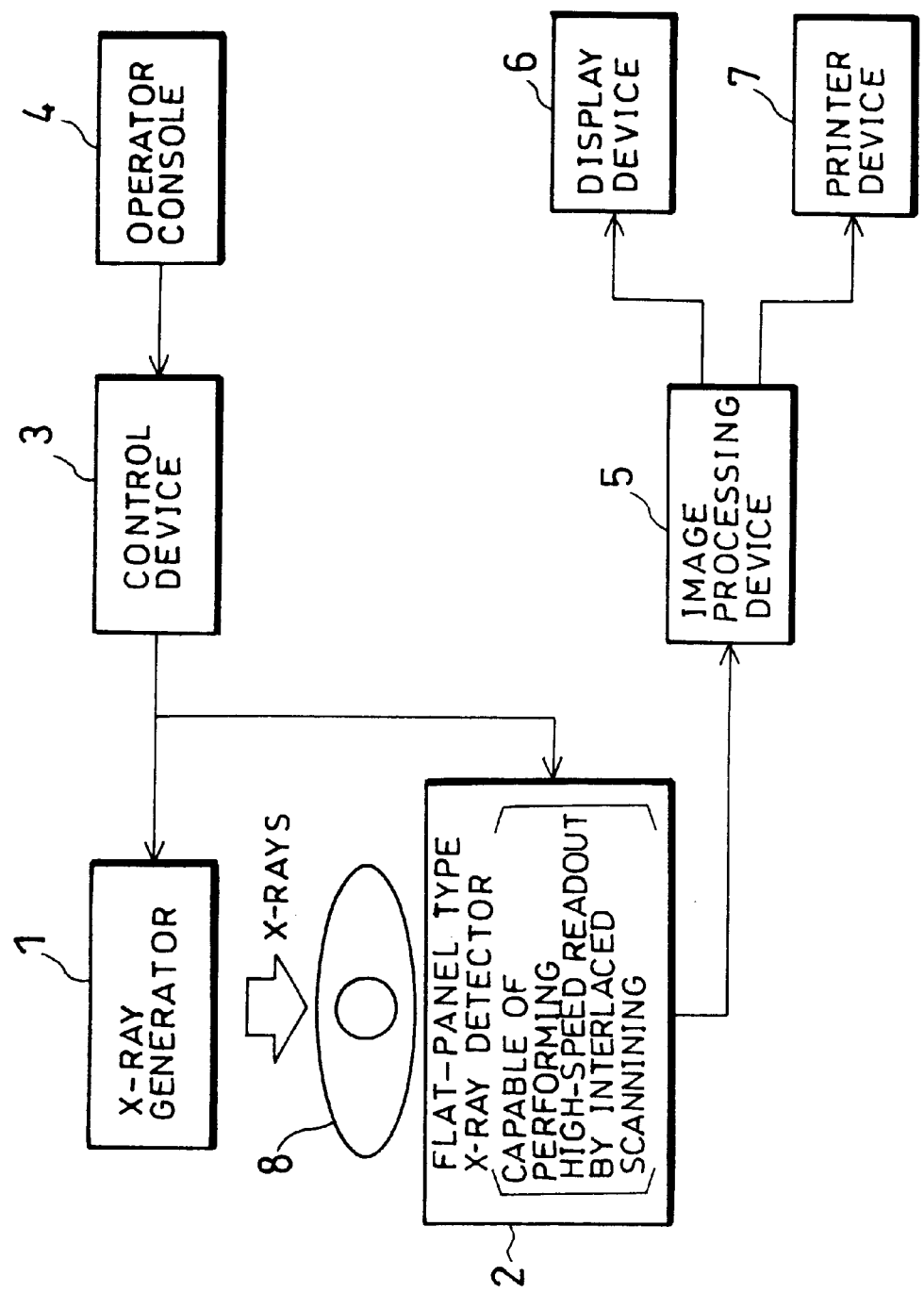
FIG. 2 is a block diagram showing a schematic structure of the X-ray imaging apparatus.

FIG. 2 shows a schematic structure of an X-ray imaging apparatus according to the present invention. As illustrated in FIG. 2, the X-ray imaging apparatus includes an X-ray generator 1 (X-ray irradiating means), a flat-panel type X-ray detector 2 (X-ray detecting device: hereinafter simply referred to as the "X-ray detector 2"), a control device 3, an operator console 4, an image processing device 5, a display device 6, and a printer device 7.

According to FIG. 2, it seems that the X-ray imaging apparatus of the present invention is the same as a conventional X-ray imaging apparatus, but the X-ray detector 2 performs a high-speed readout operation based on interlaced scanning. This is a significant characteristic of the present invention, and a big difference from the conventional X-ray imaging apparatus. This point will be described in detail later.

The X-ray generator 1 generates X-rays and irradiates the X-rays on a specimen 8. The X-ray detector 2 receives the X-rays passed through the specimen 8, and outputs electrical signals corresponding to the quantity of the X-rays to the image processing device 5. The detailed structure of the X-ray detector 2 will be discussed later.

The control device 3 controls the entire sequence and timing of the apparatus according to an input instruction from the operator console 4. The operator console 4 is provided with a switch for allowing an operator to instruct the irradiation start timing of X-rays, and X-ray imaging of the specimen 8 is initiated upon the operation of the operator console 4.

The image processing device 5 performs image processing, such as a gray-scale adjustment, with respect to image signals sent from the X-ray detector 2, and sends the signals to the display device 6 or printer device 7. The image processing device 5 performs, of course, the image processing function associated with the high-speed readout operation of the X-ray detector 2. This function will be explained in detail in the later-described sixth embodiment.

The display device 6 and printer device 7 displays or prints out the image corresponding to image data sent from the image processing device 5 as an image taken by the X-ray detector 2.

Therefore, when the operator operates the operator console 4 and inputs an X-ray imaging start instruction, the control device 3 activates the X-ray generator 1 upon the instruction and irradiates X-rays on the specimen 8 from the X-ray generator 1. When the X-rays pass through the specimen 8 and are incident on the X-ray detector 2, the X-rays are converted into electrical image signals corresponding to the quantity of the X-rays in the X-ray detector 2. The image signals are sent to the image processing device 5, subjected to image processing, such as a gray-scale adjustment, and then sent to the display device 6 and/or the printer 7. An image corresponding to the input image data is displayed on the display device 6, and the image corresponding to the image data is printed out by the printer device 7, if necessary.

Next, the following description will explain the detailed structure of the X-ray detector 2.

Figure 3:
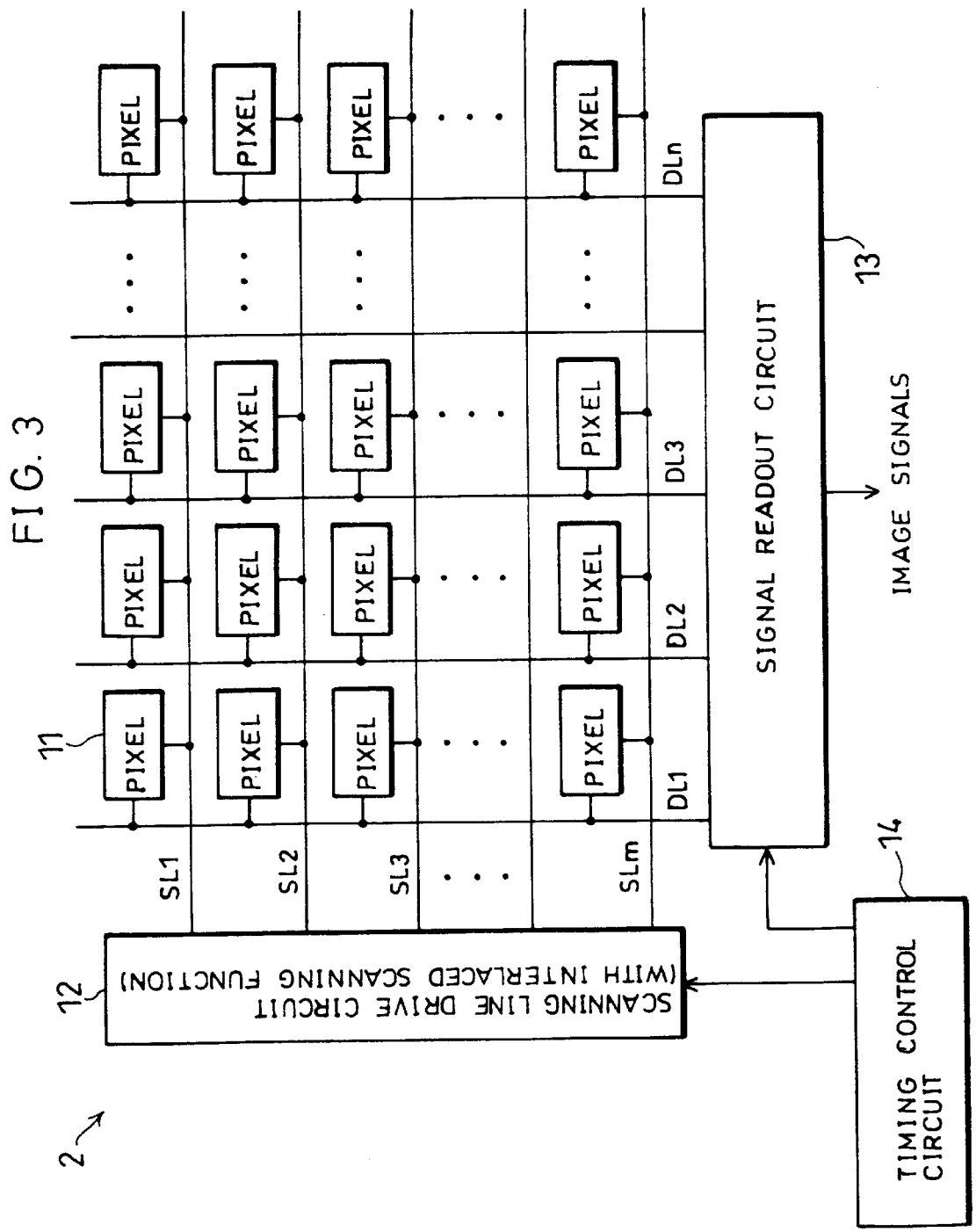
FIG. 3 is a block diagram showing the structure of an X-ray detector in the X-ray imaging apparatus.

FIG. 3 shows a schematic structure of the X-ray detector 2. As illustrated in FIG. 3, the X-ray detector 2 includes a plurality of pixels 11 arranged in a matrix form. Each pixel 11 is connected to a scanning line SLj (j=1 to m: m is an integer of not less than 2) through a gate electrode of a TFT (not shown) as a switching element and to a signal line DLi (i=1 to n: n is an integer of not less than 2) through the source electrode of the TFT.

Figure 21:
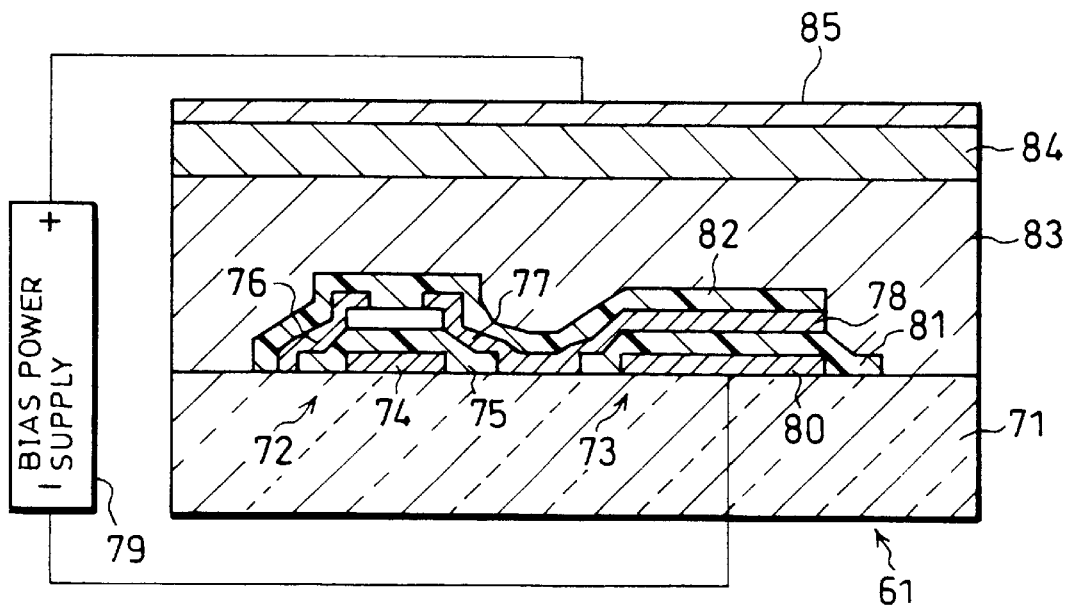
FIG. 21 is a cross sectional view showing a structure of a pixel section of the X-ray detector.
Figure 22:
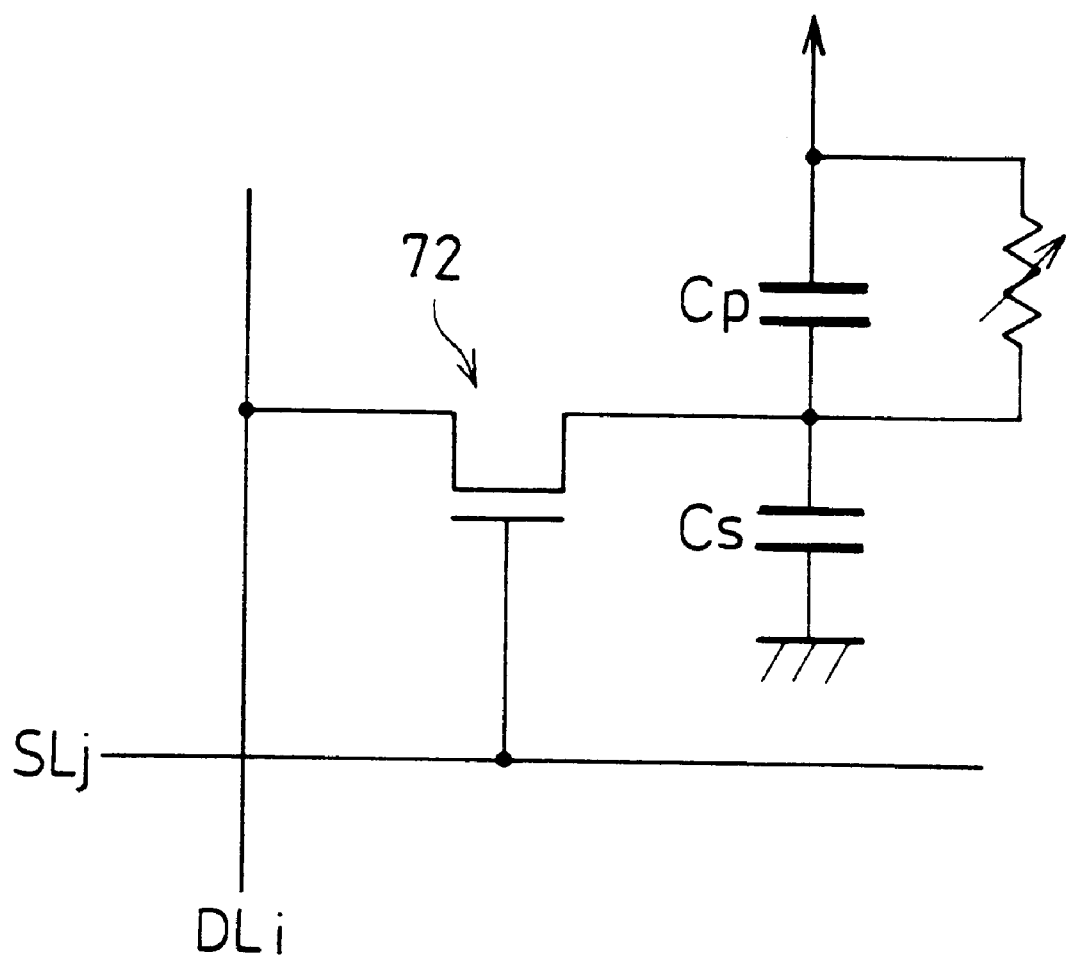
FIG. 22 is an explanatory view showing an equivalent circuit of the pixel section.

The structure and equivalent circuit of each pixel 11 of the X-ray detector 2 are the same as those of the conventional apparatus shown in FIGS. 21 and 22, and therefore the illustration and explanation thereof will be omitted here. Like the conventional apparatus, by using an amorphous silicone (s-Si) TFT as the switching element in the pixel section, sufficient ON and OFF characteristics can be obtained.

Besides, a photoconductive film and a storage capacitor of each pixel 11 form an X-ray detecting element which converts the X-rays from the specimen 8 (see FIG. 2) into charge and stores the charge.

As illustrated in FIG. 3, the scanning lines SLj are connected to a scanning line drive circuit 12 capable of performing sequential scanning and interlaced scanning, while the signal lines DLi are connected to a signal readout circuit 13. The TFTs are driven row by row through the corresponding scanning lines SLj by the scanning line drive circuit 12. Moreover, charge signals output to the signal lines DLi from the X-ray detecting elements through the TFTs are converted into voltages and read out, column by column, by the signal readout circuit 13. The charge signals are output as image signals to the image processing device 5 from the signal readout circuit 13. The scanning line drive circuit 12 and signal readout circuit 13 are controlled by a timing control circuit 14.

As the signal readout circuit 13, a conventional technique can be basically used. The signal readout circuit 13 of this embodiment has the structure shown in FIG. 4. Specifically, the signal readout circuit 13 includes pre-amplifiers 15 (integrating circuits), an amplifying circuit 16 (the amplification factor is switchable), multiplexers 17, A/D converters 18, and a buffer memory 19.

Figure 5:
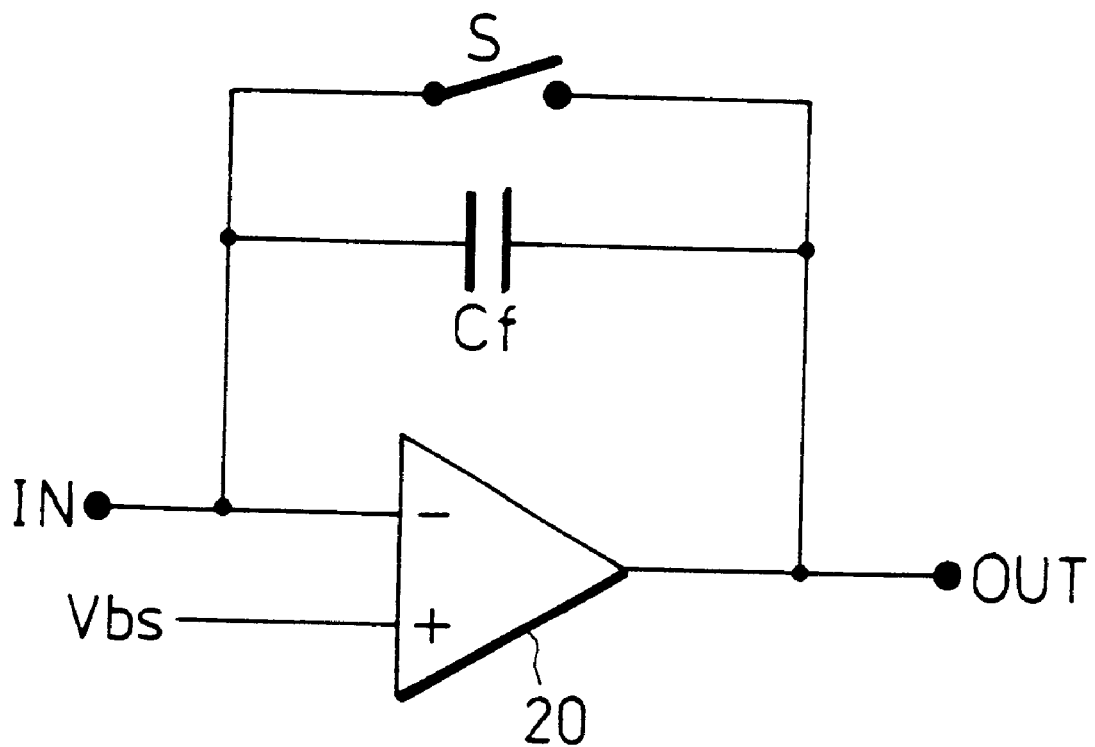
FIG. 5 is a circuit diagram showing a structure of a pre-amplifier of the signal readout circuit.
Figure 6:
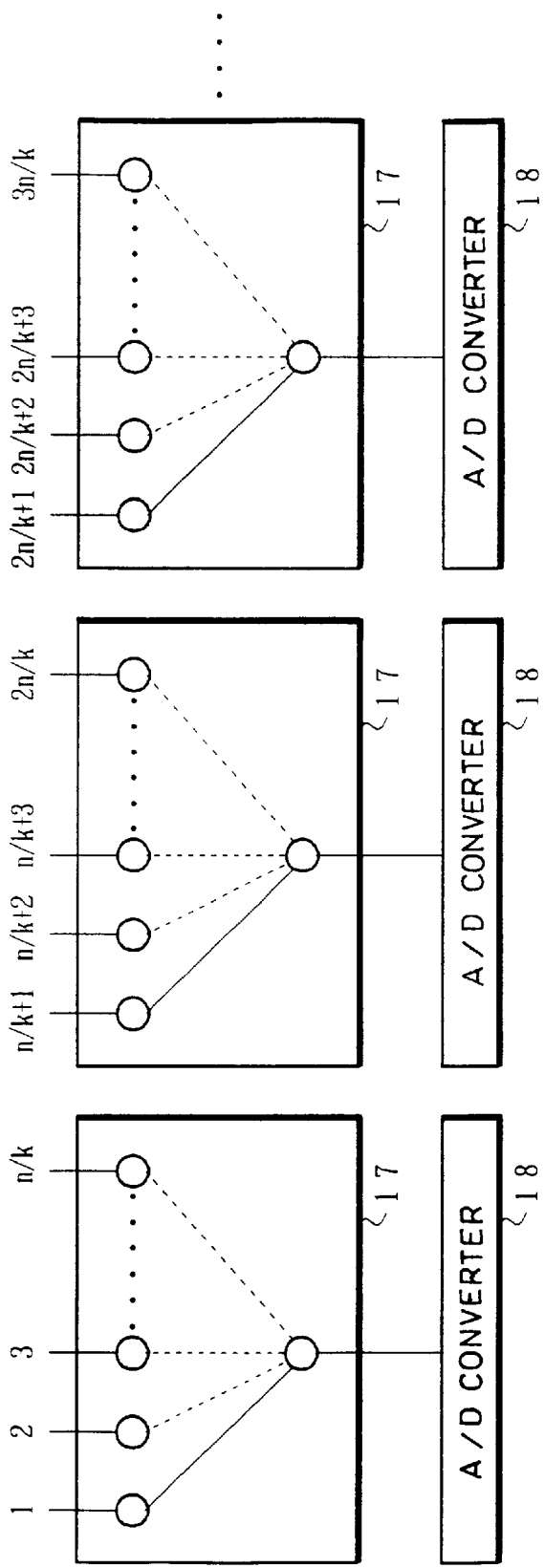
FIG. 6 is a block diagram showing a structure of a multiplexer of the signal readout circuit.

The pre-amplifiers 15 are provided in association with the respective signal lines DLi, and perform voltage conversion and amplification of the input signals. As shown in FIG. 5, each pre-amplifier 15 is formed by an operational amplifier 20 and a feedback capacitor Cf. The inverted input terminal of the operational amplifier 20 is the input of each signal line DLi, while a non-inverted input terminal is the input of an offset adjustment voltage Vbs. The feedback capacitor Cf is provided between the inverted input terminal and output terminal of the operational amplifier 20.

With this structure, charge Q input to the operational amplifier 20 is all stored in the feedback capacitor Cf, converted into a voltage V (=Q/Cf) and output. Thus, even if the charge signal is very small, it is possible to detect the charge signal with high sensitivity.

Furthermore, each pre-amplifier 15 has a switch S arranged in parallel with the feedback capacitor Cf, and can be reset by switching on the switch S.

Figure 4:
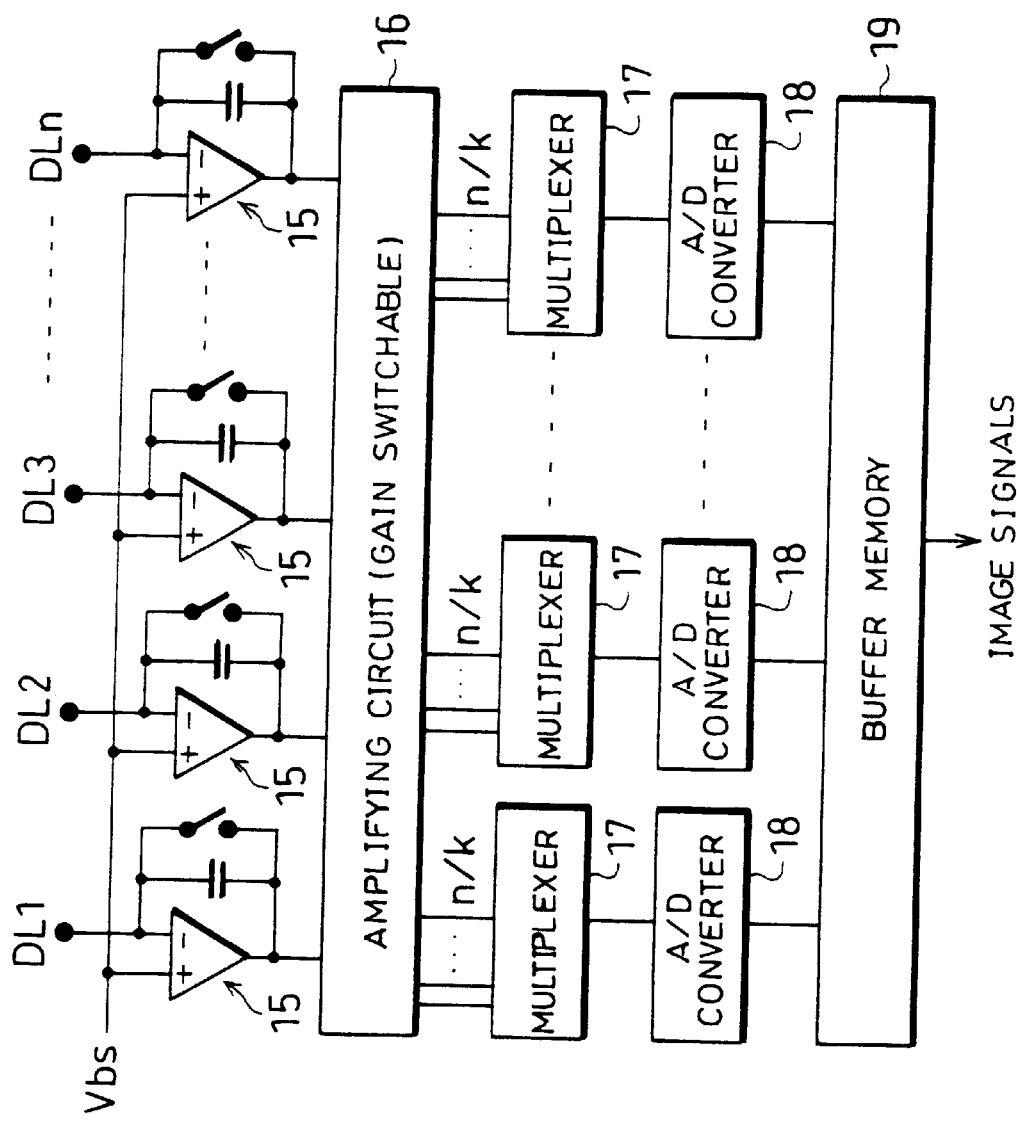
FIG. 4 is an explanatory view showing a structure of a signal readout circuit of the X-ray detector.

The amplifying circuit 16 shown in FIG. 4 further amplifies the outputs from the pre-amplifiers 15, and allows switching of gain. The amplifying circuit 16 is designed to be gain switchable for the following reasons.

The input voltage range of the A/D converters 18 disposed in the later stage of the amplifying circuit 16 are generally between, for example, 0 and 1 V, 0 and 2 V, or 0 and 5 V. The A/D converters 18 perform A/D conversion of the input voltage within such a range. Meanwhile, the quantity of X-rays per frame is around 300 $\mu$R on average in the radiography mode, and around 1 μR on average in the fluoroscopy mode. Since the signal quantity is substantially proportional to the quantity of X-rays, there is a two-digit-scale difference in the signal quantity between these modes. Therefore, in order to accurately perform A/D conversion in each mode, it is necessary to adjust the input voltages of the A/D converters 18 according to the respective modes.

Hence, by inputting the outputs from the pre-amplifiers 15 to the A/D converters 18 through the gain switchable amplification circuit 16, since the gain of the input voltage is adjusted in the amplifying circuit 16, it is possible to adjust the input voltage to fall within an input voltage range of the A/D converters 18 corresponding to each mode.

Thus, by inserting the gain switchable amplifying circuit 16 in the front stage of the multiplexers 17, it is possible to realize both the radiography mode and fluoroscopy mode, i.e., achieve these modes with accuracy.

The multiplexers 17 switch the outputs from the pre-amplifiers 15 obtained through the amplifying circuit 16 consecutively to the A/D converters 18. In this embodiment, for example, k pieces (k is an integer of not less than 2) of multiplexers 17 are provided. Moreover, the A/D converters 18 convert analog image signals from the multiplexers 17 into digital image signals, and k pieces of A/D converters 18 are provided in association with the multiplexers 17, respectively.

Figure 20:
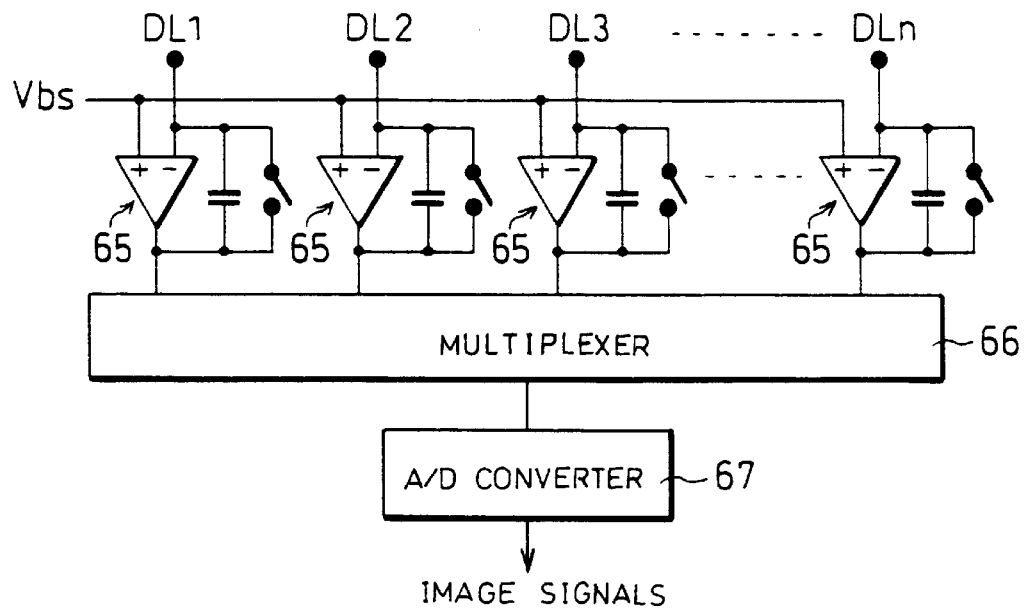
FIG. 20 is an explanatory view showing a structure of a signal readout circuit of the X-ray detector.

In the conventional structure shown in FIG. 20, the A/D conversion of the signals from the signal lines DL1 to DLn is performed using only one A/D converter 67. Therefore, in order to complete the conversion within a certain time, it is essential to form the A/D converter 67 by a converter capable of performing high-speed conversion.

However, in the structure of this embodiment shown in FIG. 4, since the A/D conversions are performed parallel by k pieces of A/D converters 18, the conversion speed of a single A/D converter 18 can be 1/k of the structure shown in FIG. 20. In this case, the output signals of n/k pieces of amplifiers are input to the multiplexers 17, and consecutively switched to the A/D converters 18 in the next stage.

Thus, unlike the conventional structure, by providing a plurality of multiplexers 17 and A/D converters 18, it is possible to shorten the overall conversion speed of the A/D converters 18 compared with the conventional structure, without forming the A/D converters 18 by special converters (capable of performing high-speed conversion). Hence, the structure of this embodiment can easily cope with high-speed processing particularly in the fluoroscopy mode.

The buffer memory 19 recombines the digital image signals from the A/D converters 18 (combines a plurality of input signals into one signal). Here, for example, assuming that k is a divisor of n, signals input to the first-stage multiplexer 17 are 1, 2, 3, ... n/k, signals input to the second-stage multiplexer 17 are n/k+1, n/k+2, n/k+3, ... 2n/k, signals input to the third-stage multiplexer 17 are 2n/k+1, 2n/k+2, 2n/k+3, ... 3n/k, and an ordinal number is added to each input signal input to the kth-stage multiplexer 17. In this embodiment, since a line of data (n words) is divided into k pieces and processed, the A/D conversions of the signals are performed in the order [1, n/k+1, 2n/k+1, 3n/k+1, ... ], [2, n/k+2, 2n/k+2, 3n/k+2, ... ] in the A/D converters and stored in the buffer memory 19 (see FIG. 4). The brackets [] means that the signals in the brackets are converted simultaneously in the A/D converter 18. Therefore, when outputting only one line of data finally, the buffer memory 19 rearranges the order of one line of data by changing the order of reading out the signals (data), and outputs the data as the image signals.

Figure 7:
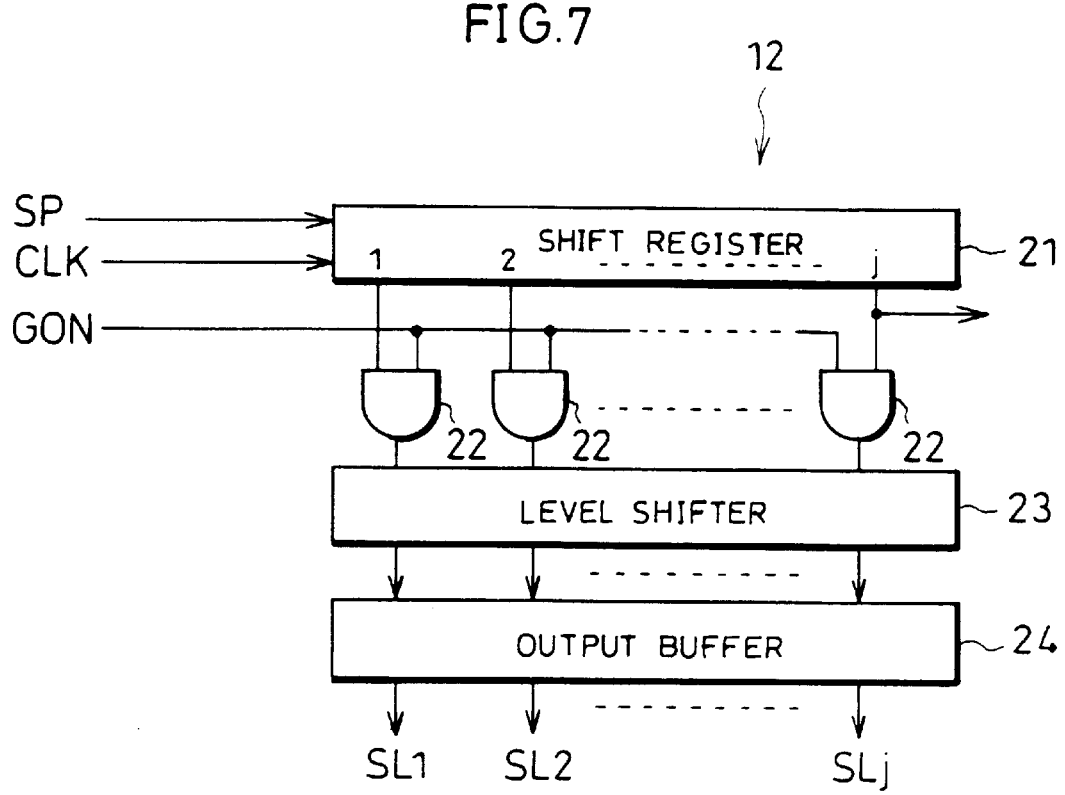
FIG. 7 is a block diagram showing a structure of a scanning line drive circuit of the X-ray detector.

Next, the following description will explain the structure and operation of the scanning line drive circuit 12 as a characteristic of the present invention. As mentioned above, the scanning line drive circuit 12 of the present invention differs significantly from the conventional structure because it performs not only the sequential scanning function, but also the interlaced scanning function. As illustrated in FIG. 7, the scanning line drive circuit 12 includes a shift register 21, a plurality of AND circuits 22, a level shifter 23, and an output buffer 24 for driving the scanning lines SLj. Thus, for example, the scanning line drive circuit 12 is capable of performing sequential scanning of scanning lines in the radiography mode (first imaging mode) for imaging a static specimen, and interlaced scanning of scanning lines in the fluoroscopy mode (second imaging mode) for imaging a dynamic specimen.

The shift register 21 generates scanning timing of each row, according to a start pulse SP and clock CLK input from the timing control circuit 14. The AND circuits 22 are provided in association with the respective rows, carry out the logical AND between the output from the shift register 21 and a GON signal for making the output from the scanning line drive circuit 12 effective, and output the logical AND to the level shifter 23. The level shifter 23 converts the output (voltage) from each AND circuit 22 from the logic level into a level necessary for driving the scanning line.

Figure 1:
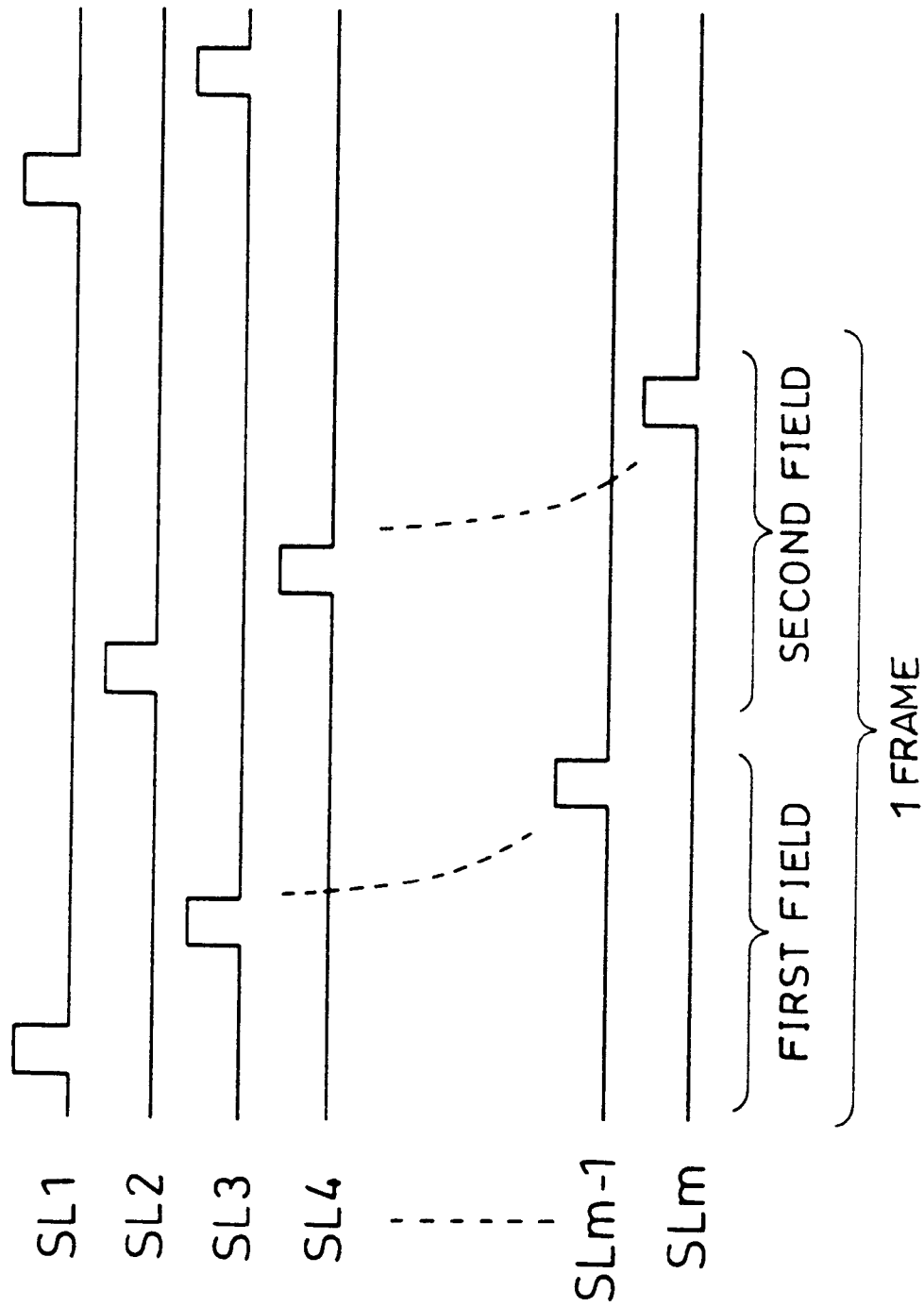
FIG. 1 is a timing chart of output waveforms of a scanning line drive circuit when interlaced scanning of scanning every other scanning line is performed in an X-ray imaging apparatus according to one embodiment of the present invention.
Figure 8:
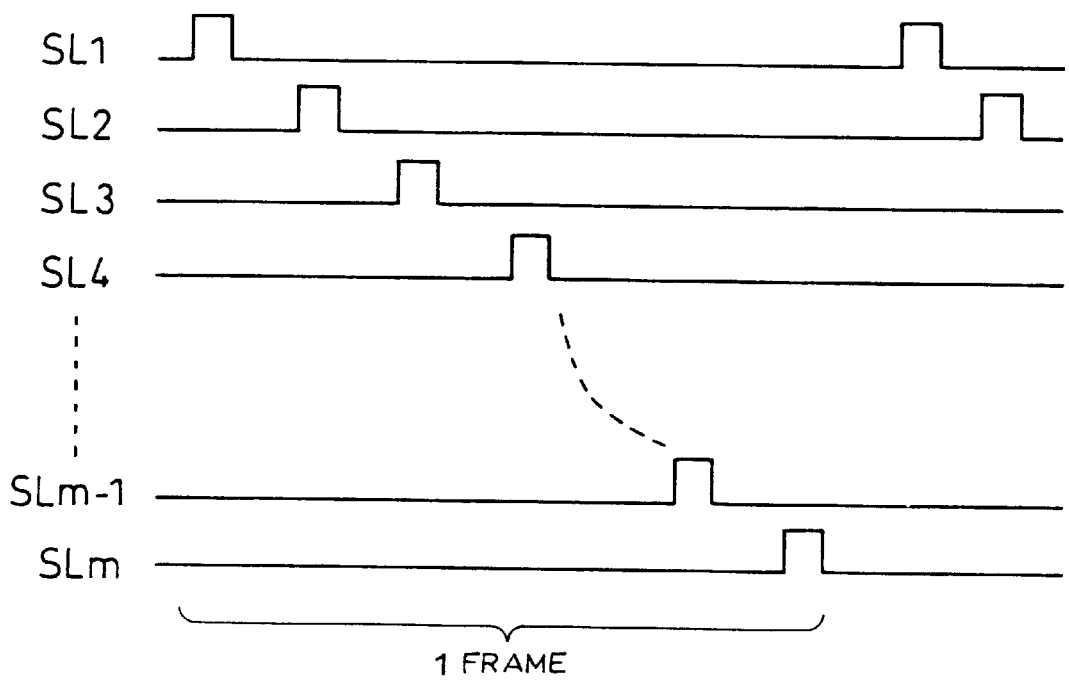
FIG. 8 is a timing chart of output waveforms of a scanning line drive circuit when sequential scanning of the scanning lines is performed.

Here, FIG. 1 shows the scanning timing of, for example, scanning in which odd-numbered scanning lines SLj are scanned sequentially in the first field, even-numbered scanning lines SLj are scanned sequentially in the second field so that all the scanning lines SLj of one frame are scanned in the first and second fields. FIG. 8 shows the timing of scanning in which the scanning lines SLj of one frame are sequentially scanned one row at a time. The scanning line drive circuit 12 of the above-mentioned structure performs, for example, the sequential scanning shown in FIG. 8 in the radiography mode, and, for example, the interlaced scanning shown in FIG. 1, if necessary, in the fluoroscopy mode. The timing necessary for each of such scanning is generated by the above-described timing control circuit 14.

On the other hand, in the case of interlaced scanning, needless to say, the even-numbered scanning lines SLj can be scanned in the first field, and then the odd-numbered scanning lines SLj are scanned in the second field. FIG. 1 shows the scanning where m is an even number.

Incidentally, since the gate driver IC incorporated into a general liquid crystal display device is usually used for the sequential scanning, it is designed without taking the interlaced scanning shown in FIG. 1 into consideration. However, if the gate driver IC has the output prohibiting function, it is possible to obtain necessary drive waveforms by modifying signals to be given.

Figure 9:
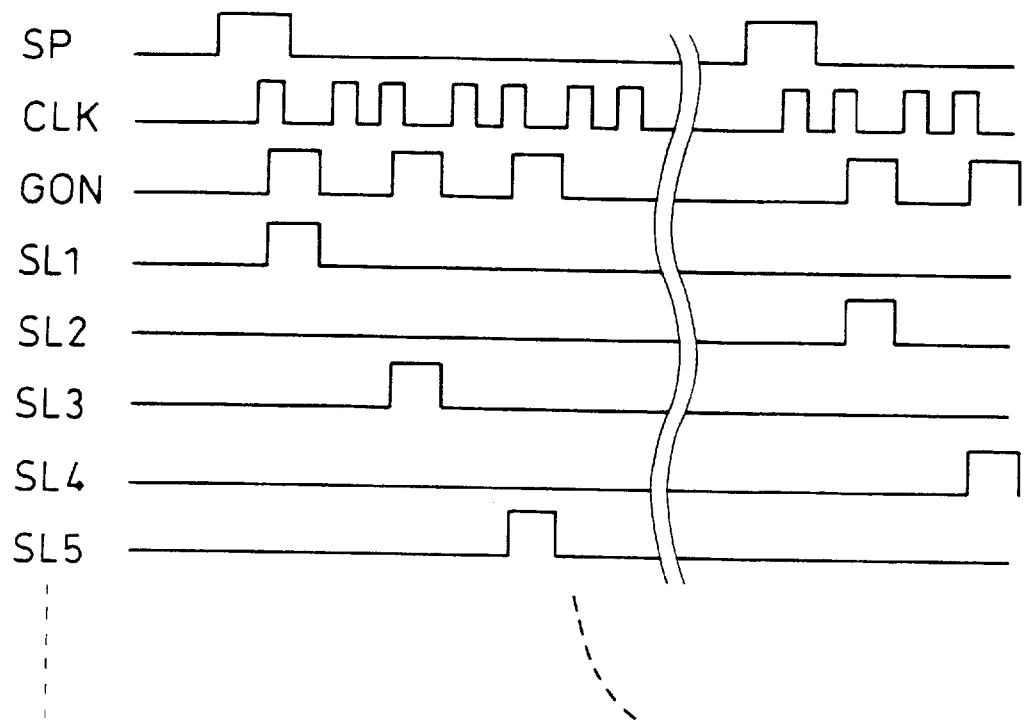
FIG. 9 is a timing chart of various signals when the scanning line drive circuit performs interlaced scanning.

The interlaced scanning by the scanning line drive circuit 12 is carried out at, for example, various timings shown in FIG. 9, under the control of the timing control circuit 14. As shown in FIG. 9, by inputting a clock CLK which are pulse signals produced at unequal intervals as clock signals into the shift register 21 and supplying a GON signal to each AND circuit 22 at intervals of, for example, two pulses of the clock CLK, it is possible to obtain output signals suitable for interlaced scanning.

The pulses of the clock CLK may be produced at equal intervals. In this case, however, the unnecessary time becomes longer, and the merit of the interlaced scanning is cancelled. In other words, in the case of FIG. 9, the time from the decay of a drive waveform of the scanning line SL1

(SL3) to the rise of a drive waveform of the scanning line SL3 (SL5) becomes excessively long, causing the same result as the sequential scanning. Such a result comes from the generation of interlaced scanning-use signals with the use of a circuit which is originally designed for sequential scanning.

Moreover, the reason why the timing of supplying the GON signal is set to two pulses of the clock CLK is that interlaced scanning is performed so as to scan every other scanning line in this embodiment (one scanning line of two scanning lines is jumped), and a desired scanning signal can not be obtained unless the GON signal is supplied at intervals of two pulses. Thus, as illustrated in the later-described third embodiment, when performing, for example, interlaced scanning of every third scanning line (scanning is performed to jump two lines of three scanning lines), the GON signal is supplied at intervals of three pulses of the clock CLK. In other words, when performing interlaced scanning to scan every (p+1)th scanning line, the GON signal is given at intervals of (p+1) pulses of the clock CLK.

Incidentally, the method for achieving the interlaced scanning is not necessarily limited to those mentioned above. For instance, it is possible to use other methods such as a method using two systems of shift registers.

Figure 10:
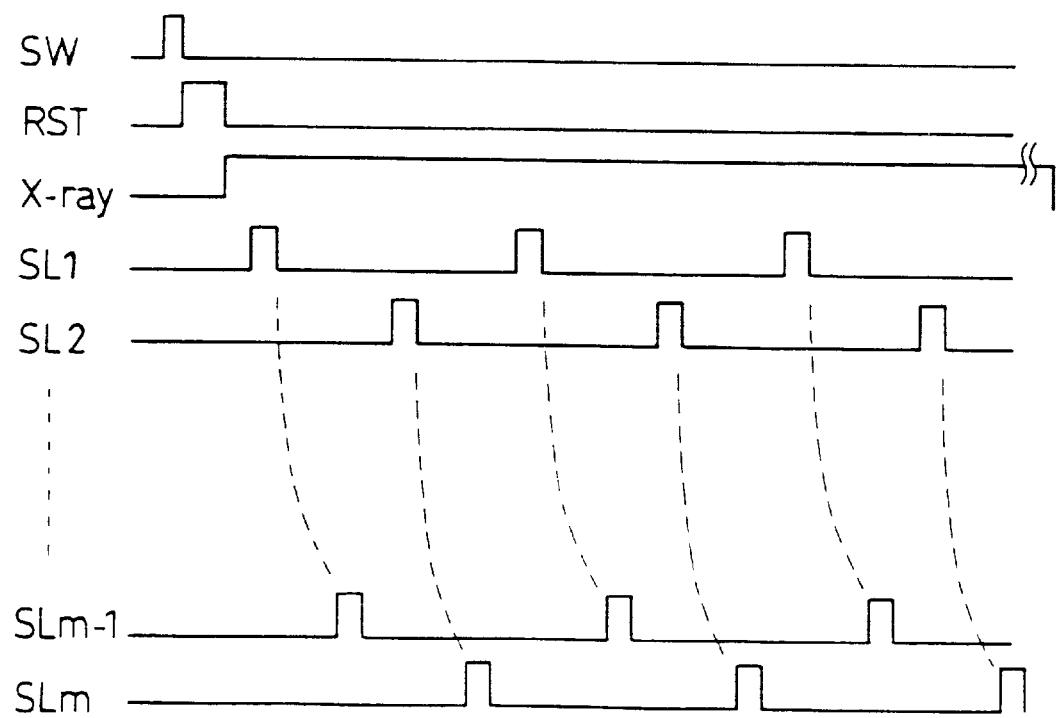
FIG. 10 is a timing chart of various signals when an X-ray generator performs continuous irradiation of X-rays on a specimen.
Figure 11:
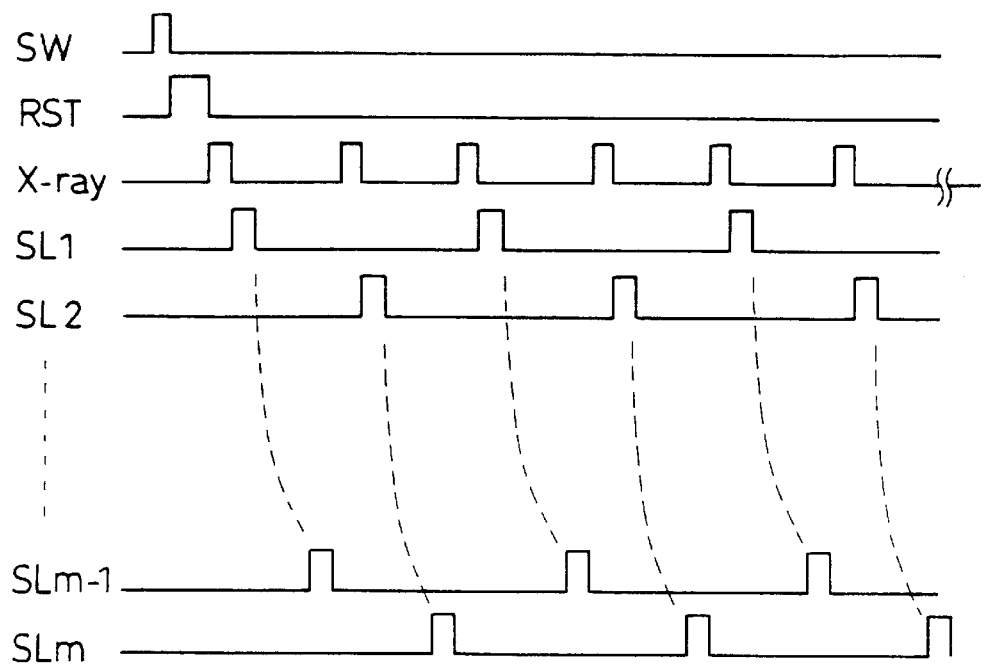
FIG. 11 is a timing chart of various signals when the X-ray generator performs pulse irradiation of X-rays on a specimen.

FIGS. 10 and 11 show an example of a sequence of X-ray irradiation when performing the interlaced scanning shown in FIGS. 1 and 9. More specifically, FIG. 10 shows a sequence of continuous X-ray irradiation of the specimen 8 (see FIG. 2), and FIG. 11 shows a sequence of pulse irradiation of X-rays for each field. In these figures, signals SW, RST and X-ray indicate the timing of pressing the switch of the operator console 4 (see FIG. 2) by the operator, the timing of initialization performed by the X-ray detector 2, and the period of X-ray irradiation, respectively.

Figure 12:
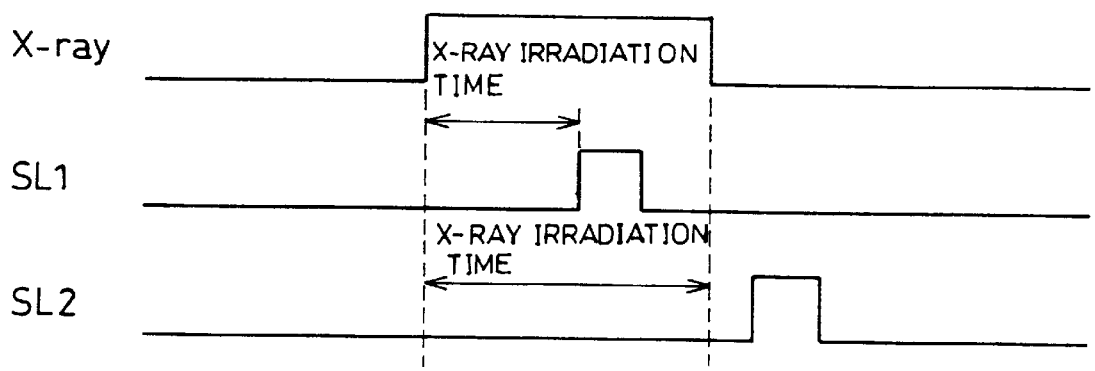
FIG. 12 is a timing chart of various signals when a pulse irradiation timing and a scanning timing for signal readout overlap in performing pulse irradiation of X-rays.

When performing the pulse irradiation shown in FIG. 11, in order to unify the signal readout condition, it is necessary to arrange the timing of pulse irradiation and the scanning timing for signal readout not to overlap each other. When these timings overlap each other, for example, as shown in FIG. 12, the X-ray irradiation time varies depending on the positions of the scanning lines, resulting in a variation in the quantity of X-rays (signal quantity).

Therefore, in the case of pulse irradiation, the cycle of one frame is longer than that of the continuous irradiation by an amount corresponding to the difference between the timings. Thus, in order to shorten the cycle of one frame, it can be said that continuous irradiation of X-rays shown in FIG. 10 is more advantageous. However, even when the pulse irradiation is performed, the effect of the present invention is, of course, obtained by interlaced scanning of the scanning lines SLj.

Next, the following description will explain the effect of providing a good signal-to-noise ratio by limiting an increase in the variation of charge on the signal line side during the transition of the scanning line voltage by the above-mentioned interlaced scanning of the scanning line drive circuit 12.

Figure 13:
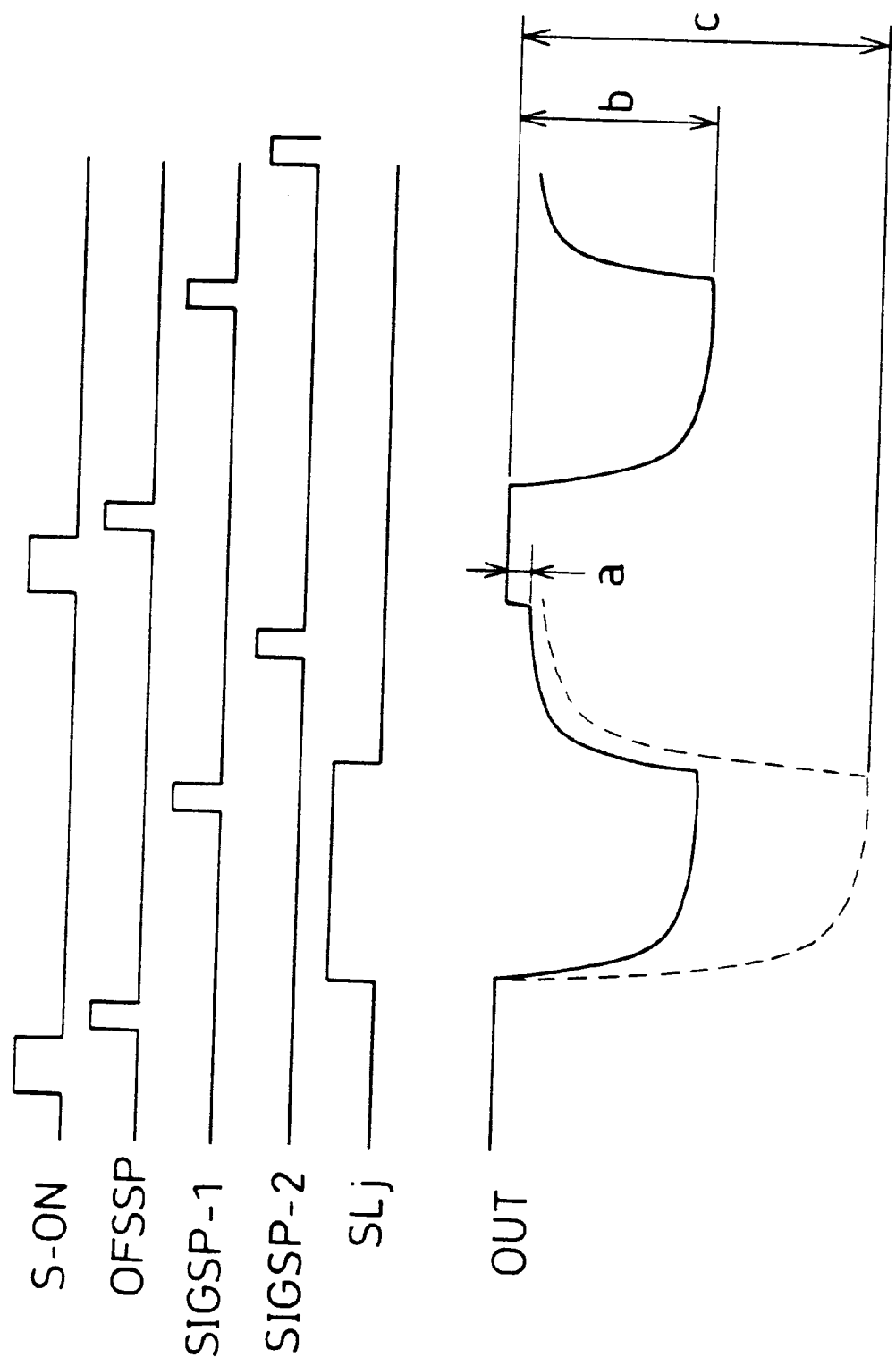
FIG. 13 is an explanatory view showing how an output waveform of the pre-amplifier shown in FIG. 5 changes during a transition of a scanning line voltage.

FIG. 13 shows an example of a pre-amplifier output waveform during signal readout when a charge amplifier with a reset function shown in FIG. 5 is used as the pre-amplifier 15 of the signal readout circuit 13. In FIG. 13, signals S-ON, OFSSP, SIGSP-1(2), SLj and OUT represent the reset timing of the pre-amplifier 15, timing of offset sampling, timing of signal sampling, drive timing of scanning line SLj, and pre-amplifier output waveform, respectively. Incidentally, SIGSP-1 shows the timing of fetching the signal when SLj is in an ON state, while SIGSP-2 shows the timing of fetching the signal after SLj changes into an OFF state. It is possible to use either of the timings.

The change of the pre-amplifier output OUT during the transition of the voltage of the scanning line SLj is caused by the above-mentioned movement of charge due to the parasitic capacitance between the scanning line SLj and signal line DLi. As illustrated qualitatively in FIG. 13, a signal quantity a obtained in the fluoroscopy mode is much smaller than a charge variation b during the transition of the scanning line voltage. Therefore, for example, if only the frame frequency is increased without changing the quantity of X-rays irradiated per unit time, the signal quantity is further decreased, resulting in deterioration of the signal-to-noise ratio.

Hence, in prior arts, a method of increasing the amount of signal charge by, for example, driving a plurality of scanning lines SLj simultaneously, instead of sacrificing the resolution, has been employed. However, when a plurality of scanning lines are driven simultaneously, as shown by the broken line of FIG. 13, the variation of charge during the transition of the scanning line voltage is increased depending on the number of the simultaneously driven scanning lines SLj (as shown by c in FIG. 13). Here, the broken line shows an example of the waveform of pre-amplifier output OUT when two scanning lines are driven simultaneously.

Against such an increase in the variation of charge during the transition of the scanning line voltage, when fetching the signal at the timing of SIGSP-1, it is necessary to significantly change the offset adjustment. On the other hand, when fetching the signal at the timing of SIGSP-2, it is necessary to delay the time of sampling until the effect of the variation of charge during the transition of the scanning line voltage is reduced. Moreover, fluctuations in the voltage on the scanning line side is one of the main causes of noise, and the noise is increased by simultaneous driving of a plurality of scanning lines SLj.

Here, when the quantity of X-rays irradiated per unit time is uniform in the fluoroscopy mode, the resolution in a time axis direction, the signal quantity, the resolution in a vertical direction and the variation of charge during the transition of the scanning line voltage of the three scanning modes (sequential scanning, two-line simultaneous scanning (prior art), interlaced scanning) were compared relatively with reference to the sequential scanning, and the results are shown in Table 1.

TABLE 1

|  | Frame frequency [Hz] | Resolution in time axis direction (relative value) | Signal quantity (relative value) | Resolution in vertical direction (relative value) | Variation of charge (relative value) |
| --- | --- | --- | --- | --- | --- |
| Sequential scanning | 30 | 1 | 1 | 1 | 1 |
| Two-line Simultaneous scanning | 60 | 2 | 1 | 0.5 | 2 |
| | 30 | 1 | 2 | 0.5 | 2 |
| Interlaced scanning | 30 | about 1.5 | 1 | 0.5 to 1 | 1 |

It should be understood from Table 1 that the resolution in a time axis direction or the signal quantity can be increased according to the frame frequency by scanning two scanning lines simultaneously to sacrifice the resolution in a vertical direction. However, the variation of charge during the transition of the scanning line voltage is doubled. Moreover, the resolution in the vertical direction is lowered to a half in the two-line simultaneous scanning at either of the frame frequencies.

However, when interlaced scanning is performed to scan every other scanning line like the present invention and the image is updated by a unit of field, the resolution in the time axis direction is improved and an image with a vertical resolution between those of sequential scanning and two-line simultaneous scanning is obtained. Moreover, since the driving of the scanning lines SLj is performed one row at a time, the variation of charge during the transition of the scanning line voltage remains the same as that of sequential scanning.

Thus, in the present invention, by performing interlaced scanning to scan every other scanning line, it is possible to improve the resolution in the time axis direction without increasing at all the variation of charge during the transition of the scanning line voltage at the same frame frequency, by sacrificing the resolution in the vertical direction. Thus, a change of the offset adjustment and a change of timing of fetching the signal, which are necessary for two-line simultaneous scanning, are not necessary at all, and an increase of noise due to fluctuations in the voltage on the scanning line side can be avoided.

Incidentally, in the present invention, sequential scanning is performed in the radiography mode, and interlaced scanning is performed in the fluoroscopy mode. However, according to Table 1, since there is not a difference in the variation of charge between the radiography mode and the fluoroscopy mode, it can be explained that the scanning line drive circuit 12 of the present invention scans the scanning lines according to individual imaging modes so that the variation of charge of the signal line during the transition of the scanning line voltage does not change between different imaging modes of the specimen 8.

[Second Embodiment]

Figure 14:
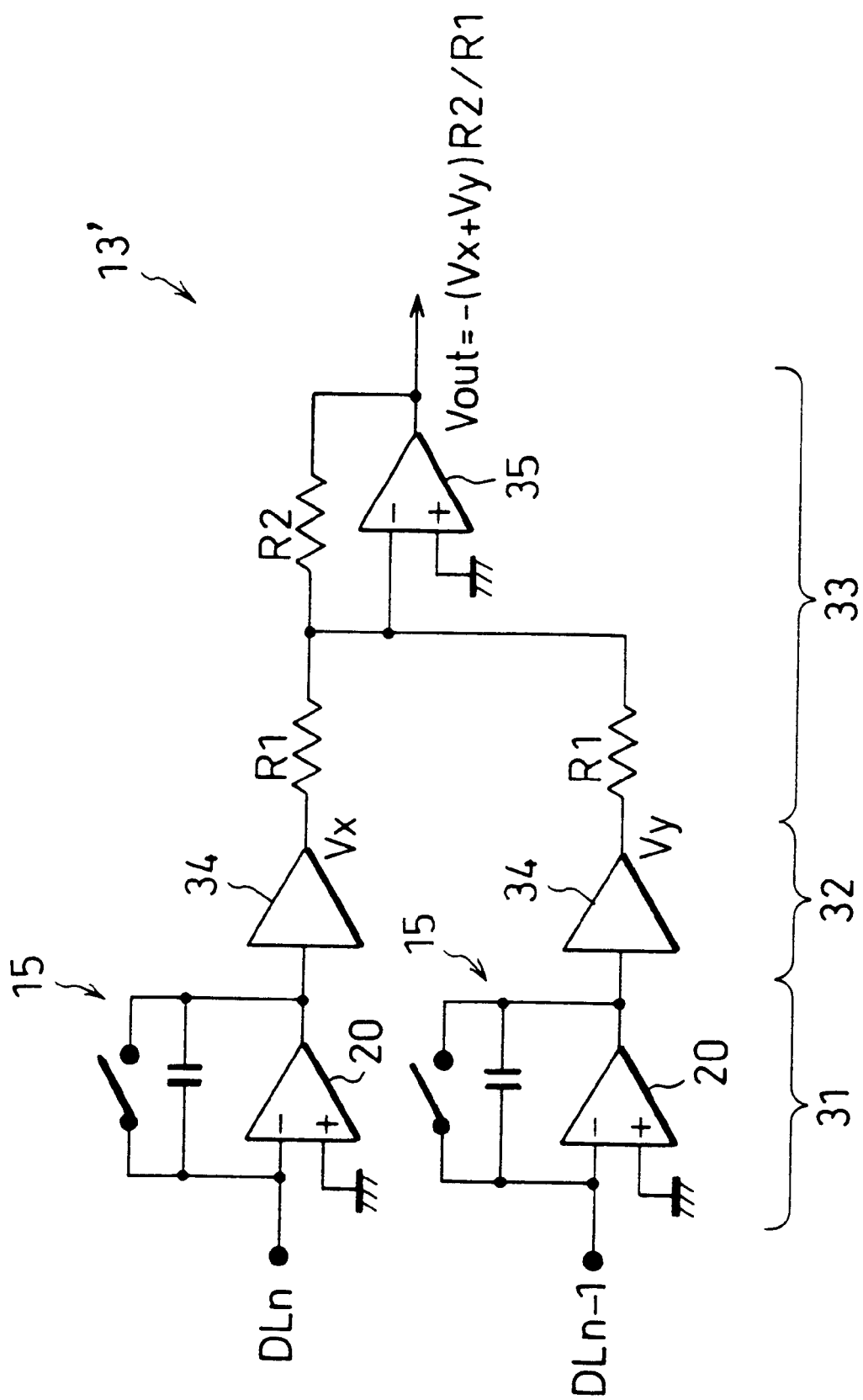
FIG. 14 is a circuit diagram showing a structure of a signal readout circuit of an X-ray imaging apparatus according to another embodiment of the present invention.

The following description will explain another embodiment of the present invention with reference to FIG. 14. For the sake of convenience of explanation, the structures having the same functions as those in the first embodiment will be designated by the same codes and the explanation thereof will be omitted.

An X-ray imaging apparatus according to this embodiment is basically the same as the apparatus of the first embodiment except that the signal readout circuit 13 of the first embodiment is replaced by a signal readout circuit 13' shown in FIG. 14. In the description below, the structure of the signal readout circuit 13' corresponding to adjacent two signal lines DLn and DLn-1 will be illustrated. However, the structure is also the same about the remaining signal lines DLi.

The signal readout circuit 13' adds the pixel signals in a horizontal direction. As illustrated in FIG. 14, the signal readout circuit 13' includes a pre-amplifier 31, a gain adjustment amplifier 32, an adder circuit 33 (addition processing circuit), an A/D converter (not shown), and a buffer memory. Namely, in the signal readout circuit 13', the pre-amplifier 15, amplifying circuit 16 and multiplexer 17 shown in FIG. 4 are replaced by the pre-amplifier 31, gain adjustment amplifier 32 and adder circuit 33.

The pre-amplifier 31 includes two pre-amplifiers 15 of the structure shown in FIG. 5. In this embodiment, however, the non-inverted input terminal of the operational amplifier 20 of each pre-amplifier 15 is ground. Moreover, the inverted input terminals of the operational amplifiers 20 are the inputs of signals from the respective signal lines DLn and DLn-1.

The gain adjustment amplifier 32 is formed by amplifier circuits 34 provided in association with the respective pre-amplifiers 15 (however, the connecting elements such as feedback resistors are not shown). Namely, the outputs from the pre-amplifiers 15 are input to the amplifier circuits 34.

The adder circuit 33 is composed of an operational amplifier 35, two resistors R1, and a resistor R2. One end of each resistor R1 is connected to the output terminal of each amplifier circuit 34, while the other end is connected to the inverted terminal of the operational amplifier 35 and one end of the resistor R2. Besides, the other end of the resistor R2 is connected to the output of the operational amplifier 35, and the non-inverted terminal of the operational amplifier 35 is ground.

According to such a structure of the analog circuit, if the output voltages of the amplifiers 34 are denoted by Vx and Vy, an output voltage Vout from the adder circuit 33 is given by $$Vout=-(Vx+Vy)R2/R1.$$

The output voltage Vout is output through the A/D converter and buffer memory in the later stages.

In the above-described first embodiment, the resolution in the vertical direction of the image signals of each field obtained by interlaced scanning is usually a half of that of sequential scanning. Like the second embodiment, by adding signals of every two signal lines (every two pixels in a horizontal direction), it is possible to arrange the resolution in the horizontal direction to be the same as the resolution in the vertical direction.

Here, it is considered that the information of the specimen 8 does not show an abrupt change spatially. Therefore, it can be said that the adjacent image signals have a very high correlation. On the other hand, thermal noise and quantum noise do not have a spacial correlation. When correlated signals (voltages) are added, a substantially doubled voltage is obtained. On the other hand, when non-correlated signals are added, the result is equivalent to the addition of electric power, and thus the electric power is increased by two times, but the voltage is increased by $\sqrt{2}$ times. Therefore, by adding the signals using the signal readout circuit 13', the signal-to-noise ratio can be improved by $2/\sqrt{2}=\sqrt{2}$ times by making the resolution in the horizontal direction equal to the resolution in the vertical direction.

Besides, as a method of improving the signal-to-noise ratio other than the use of the signal readout circuit 13', for example, there is a method of providing a digital circuit for performing addition processing after A/D conversion. There is also a method of performing arithmetic processing with a digital image processor in the image processing device 5 (see FIG. 2).

[Third Embodiment]

Figure 15:
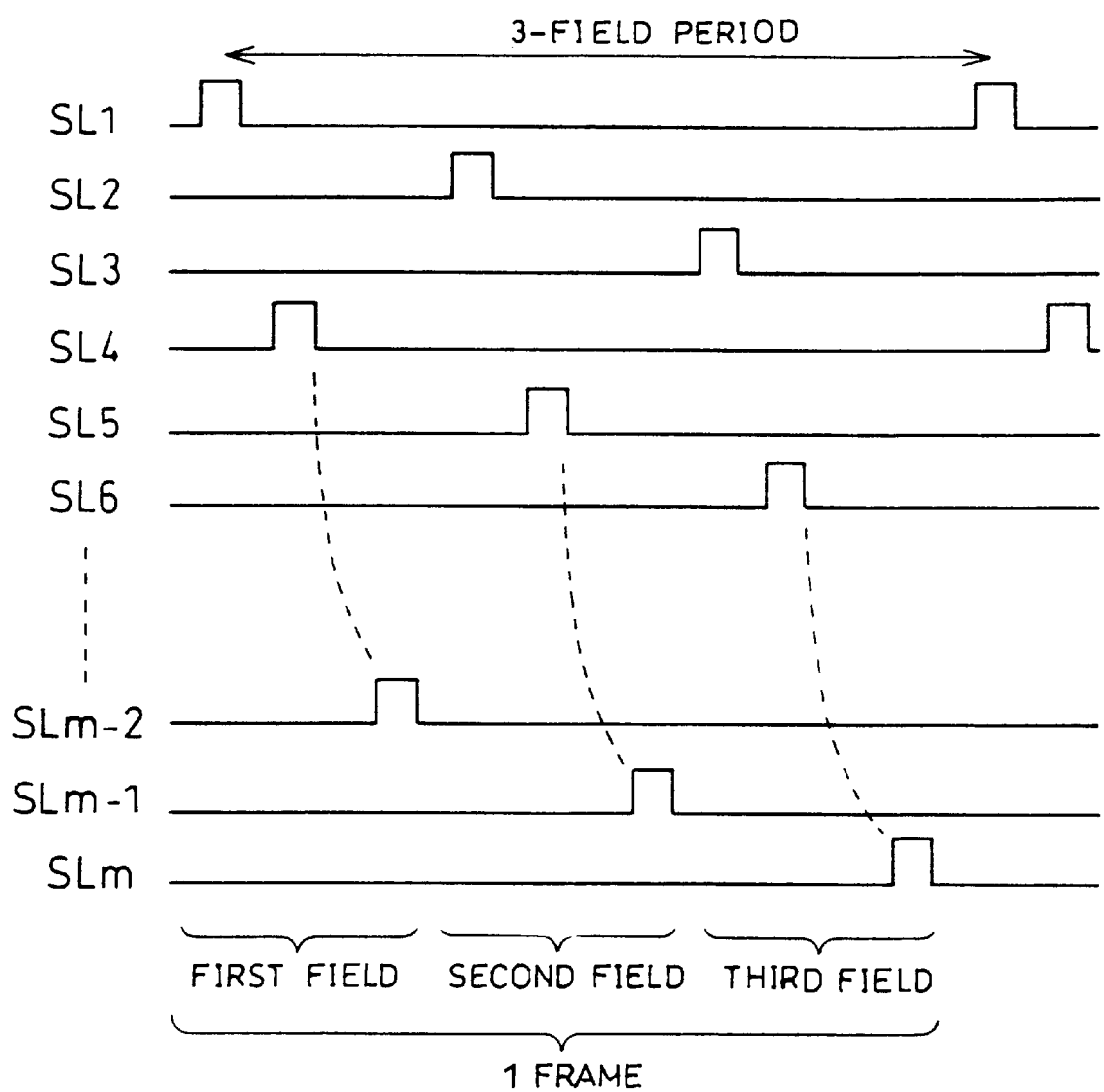
FIG. 15 is a timing chart of output waveforms of a scanning line drive circuit when interlaced scanning of scanning every third scanning line is performed in an X-ray imaging apparatus according to still another embodiment of the present invention.

The following description will explain other embodiment of the present invention with reference to FIG. 15. For the sake of convenience of explanation, the structures having the same functions as those in the first and second embodiments will be designated by the same codes and the explanation thereof will be omitted.

An X-ray imaging apparatus according to this embodiment has the same structure of that of the first embodiment except that the scanning line drive circuit 12 performs interlaced scanning to scan at intervals of a plurality of scanning lines. FIG. 15 shows an example of drive waveforms of the scanning line drive circuit 12 which performs interlaced scanning to scan every third scanning line (here, m is a multiple of 3). In FIG. 15, the (3t-2)th scanning line, the (3t-1)th scanning line and the 3tth scanning line are scanned in the first field, second field and third field, respectively (here, t is an integer of not less than 1).

Thus, by updating the image every field (in this embodiment, every ⅓ frame), if the horizontal scanning period is uniform, it is possible to make the scanning speed of one frame three times faster than the scanning speed of usual line sequential scanning. Also, in this case, if continuous irradiation of X-rays is performed, the signal quantity of one readout will not change.

On the other hand, if the field cycle is increased by three times, it is possible to obtain three times the signal quantity at the same screen scanning speed. With a prior art, when three scanning lines are scanned simultaneously, the variation of charge on the signal line side during the transition of the scanning line voltage is increased by three times. However, with the present invention, such an increase in the variation of charge does not occur at all.

The pixel pitch of the X-ray detector 2 is, for example, around 80 to 200 $\mu$m, and it is sometimes necessary to increase the signal quantity in the fluoroscopy mode or perform high-speed scanning depending on such a pixel pitch specification and applications, by further sacrificing the resolution. In such a case, the method using interlaced scanning of performing scanning at intervals of a plurality of scanning lines is extremely helpful.

In this embodiment, interlaced scanning of scanning every third scanning line is explained. However, needless to say, it is possible to scan every fourth scanning line or every fifth scanning line, if necessary. Moreover, the signal-to-noise ratio can further be improved by combining the addition processing of signals in a horizontal scanning direction like the second embodiment.

[Fourth Embodiment]

Figure 16:
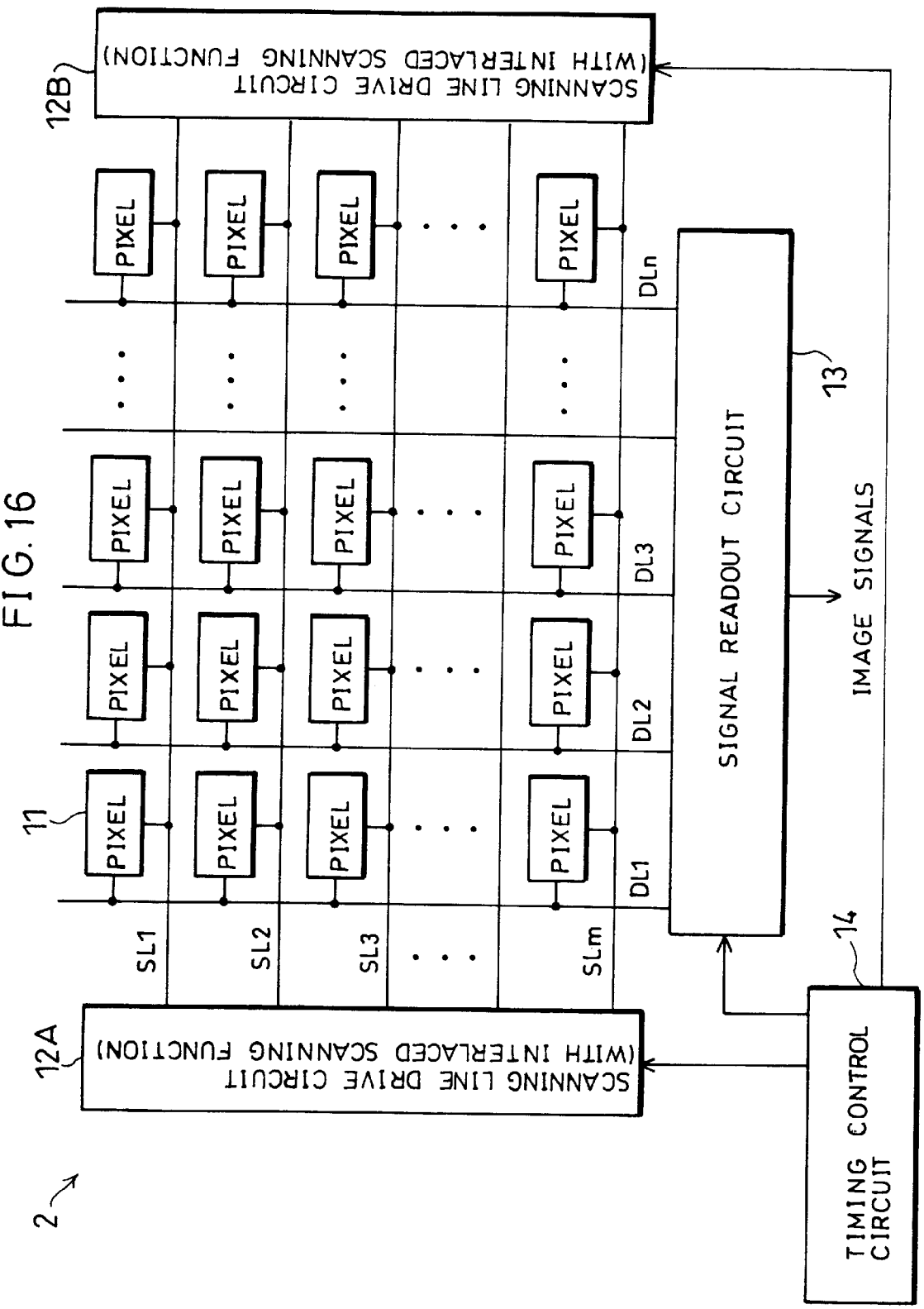
FIG. 16 is a block diagram showing a structure of an X-ray detector of an X-ray imaging apparatus according to yet another embodiment of the present invention.

The following description will explain other embodiment of the present invention with reference to FIG. 16. For the sake of convenience of explanation, the structures having the same functions as those in the first to third embodiments will be designated by the same codes and the explanation thereof will be omitted.

As illustrated in FIG. 16, an X-ray imaging apparatus according to this embodiment has the same structure as that of the first embodiment except that two scanning line drive circuits 12 of the same structure as that of the first embodiment are prepared and disposed on both ends of the scanning lines SLj to form the X-ray detector 2. For the sake of convenience of explanation, these scanning line drive circuits 12 are referred to as the scanning line drive circuits 12A and 12B. Of course, the scanning line drive circuits 12A and 12B have the above-mentioned interlaced scanning function as well as the sequential scanning function. Moreover, the scanning line drive circuits 12A and 12B are basically driven at the same timing by the timing control circuit 14.

In the case where only one scanning line drive circuit is provided, when the size of the X-ray detector 2 is increased and the number of pixels is increased, the resistance and capacitance of the scanning lines SLj are increased. As a result, the drive waveform on the scanning line at a position distant from the scanning line drive circuit is rounded, preventing uniform signal readout. In order to limit this influence, it is necessary to increase the pulse width for driving the scanning lines SLj. However, for example, if this time width is 10 $\mu$s, the time for scanning 3000 scanning lines SLj is 30 ms for sequential scanning, and 15 ms for interlaced scanning of every other scanning line. It is thus difficult to read out the signals in real-time.

However, by connecting the scanning line drive circuits 12A and 12B to both sides of the TFT array as in the fourth embodiment, it can be considered that each scanning line is substantially divided at the center thereof and driven from both sides by the scanning line drive circuits 12A and 12B.

Here, the resistance and capacitance of the scanning line are denoted by R and C, respectively, a time constant $\tau 1$ is given by $$\tau 1 = RC.$$

However, in the event in which the scanning line is divided into two parts as mentioned above, since the resistance and capacitance of a half scanning line are R/2 and C/2, respectively, a time constant $\tau 2$ is given by $$\tau 2 = (R/2) \cdot (C/2) = RC/4 = \tau 1/4.$$

Accordingly, with the structure of this embodiment, since the time constant of the scanning line SLj is substantially ¼, it is possible to limit the roundness of the drive waveform significantly. Consequently, even when the size of the X-ray detector 2 is increased and the number of pixels is increased, it is possible to achieve high-speed signal readout with low noise like the first embodiment.

[Fifth Embodiment]

Figure 17:
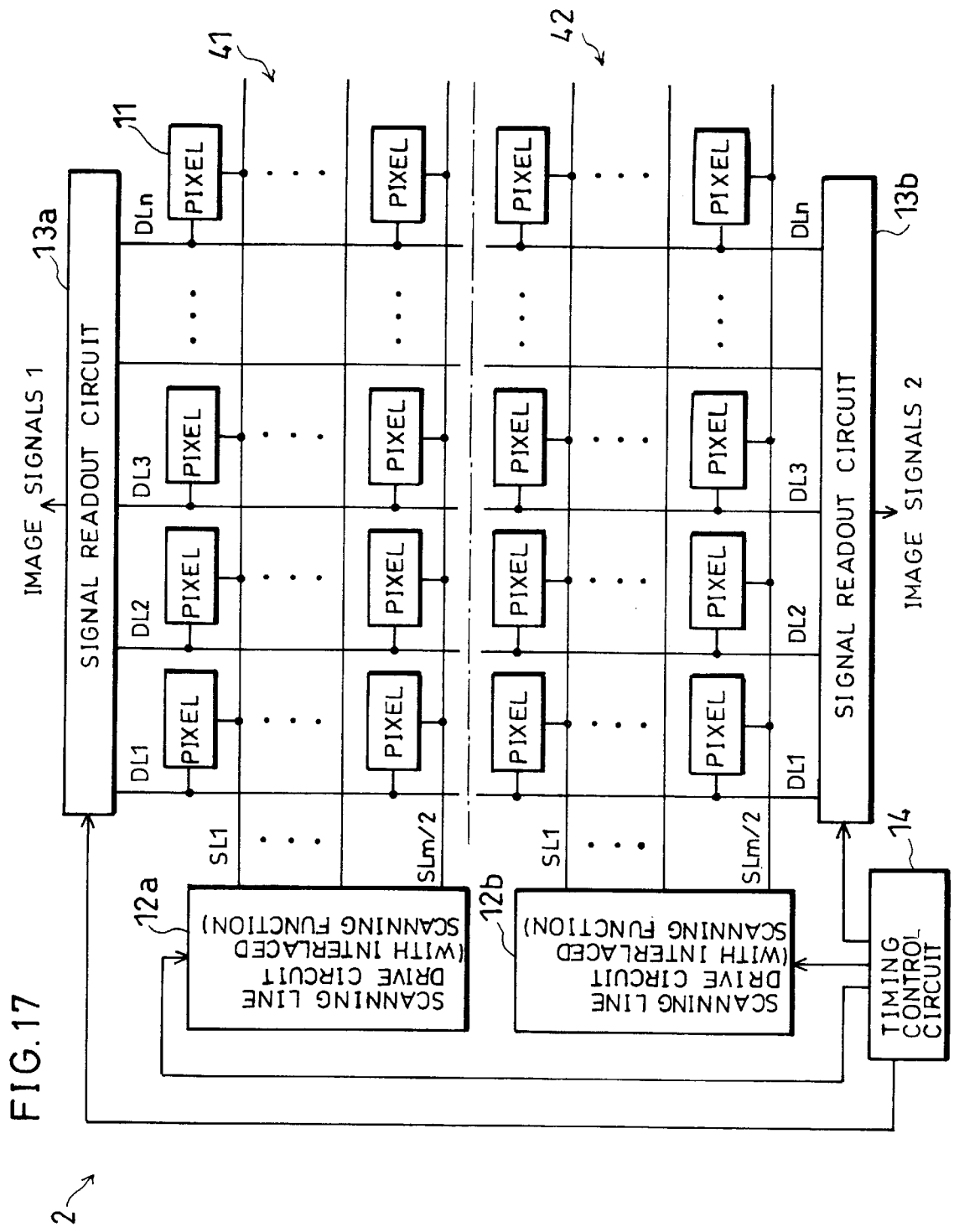
FIG. 17 is a block diagram showing a structure of an X-ray detector of an X-ray imaging apparatus according to other embodiment of the present invention.
Figure 18:
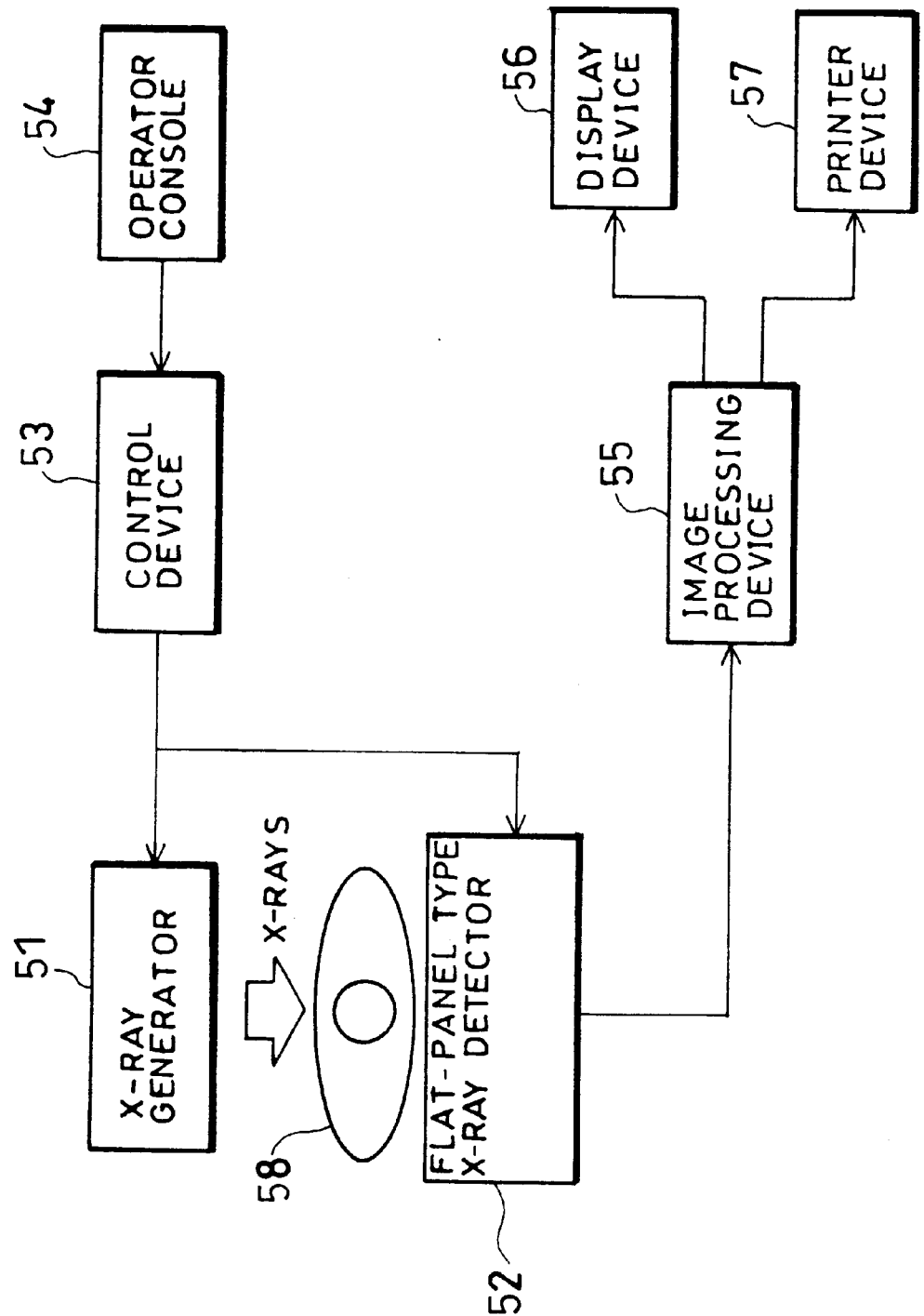
FIG. 18 is a block diagram showing a schematic structure of a conventional X-ray imaging apparatus.
Figure 19:
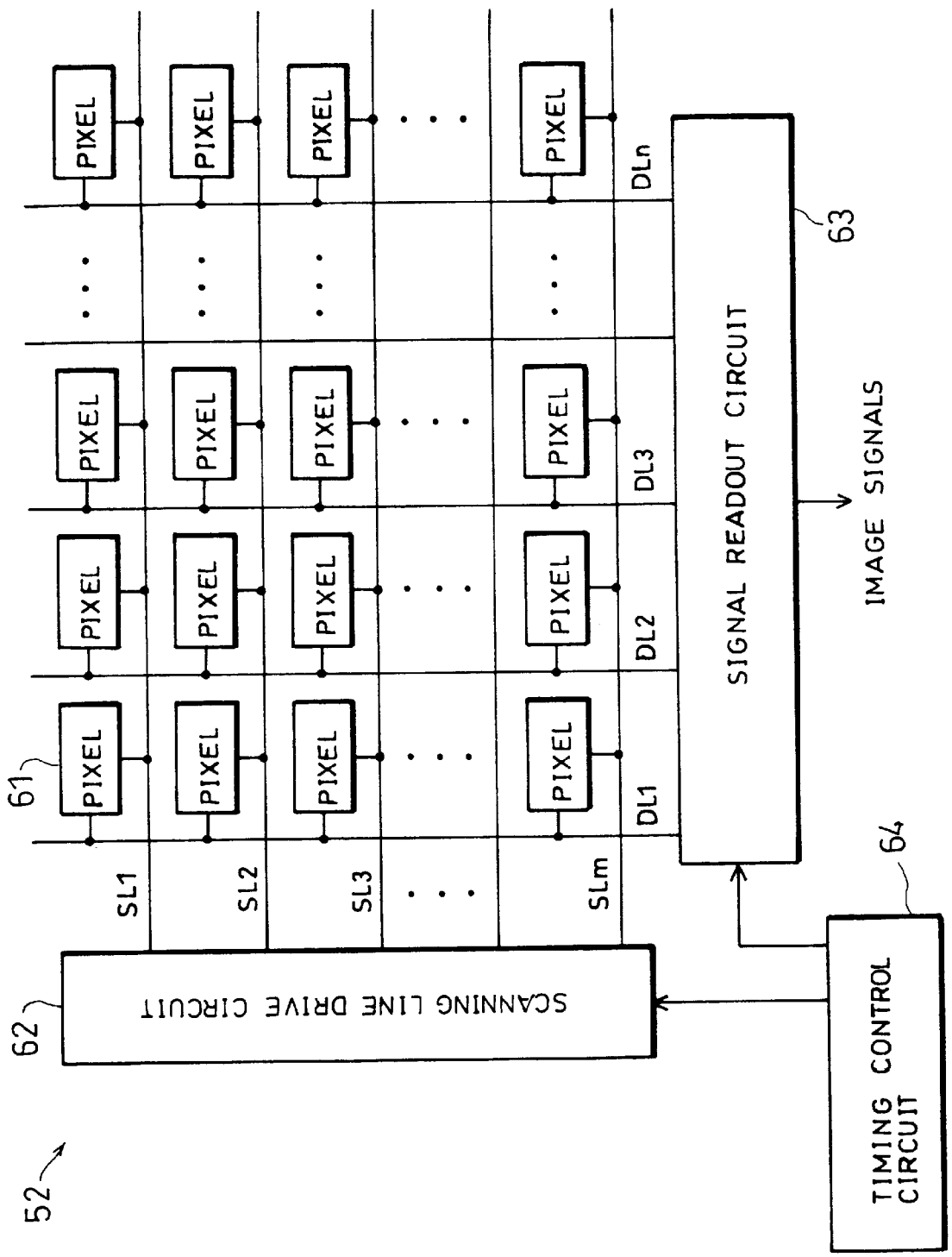
FIG. 19 is a block diagram showing a structure of an X-ray detector of the X-ray imaging apparatus.

The following description will explain other embodiment of the present invention with reference to FIG. 17. For the sake of convenience of explanation, the structures having the same functions as those in the first to fourth embodiments will be designated by the same codes and the explanation thereof will be omitted.

As illustrated in FIG. 17, an X-ray imaging apparatus according to this embodiment has the same structure as that of the first embodiment except that the X-ray detector 2 is formed by dividing each signal line DLi into upper and lower regions at the substantially center thereof (shown by the alternate one dot and one short line), and the scanning line drive circuit 12 and signal readout circuit 13 are provided in association with the divided regions 41 and 42, respectively. In FIG. 17, m is an even number. However, there is no problem even if m is an odd number.

For the sake of convenience of explanation, the scanning line drive circuit 12 and signal readout circuit 13 associated with one of the divided regions, 41, are referred to as the scanning line drive circuit 12a and signal readout circuit 13a, respectively. Similarly, the scanning line drive circuit 12 and signal readout circuit 13 associated with the other divided region, 42, are referred to as the scanning line drive circuit 12b and signal readout circuit 13b, respectively.

In short, the scanning lines SLj and signal lines DLi in the divided region 41 are respectively connected to the scanning line drive circuit 12a and signal readout circuit 13a. Meanwhile, the scanning lines SLj and signal lines DLi in the divided region 42 are respectively connected to the scanning line drive circuit 12b and signal readout circuit 13b. Of course, the scanning line drive circuits 12a and 12b have the above-mentioned interlaced scanning function as well as the sequential scanning function.

Moreover, in the fluoroscopy mode, the scanning line drive circuits 12a and 12b are basically driven in parallel at the same timing by the timing control circuit 14. It is possible to perform interlaced scanning of the scanning lines SLj in one of the divided regions in the order "odd-numbered lines→to even-numbered lines", and perform interlaced scanning of the scanning lines SLj in the other divided region in the order "even-numbered lines→to odd-numbered lines". On the other hand, in the radiography mode, it is not necessarily to drive the scanning line drive circuits 12a and 12b at the same timing. In other words, the scanning line drive circuits 12a and 12b can be driven by turn.

When the size of the X-ray detector 2 is increased and the number of pixels is also increased, not only the resistance and capacitance of the scanning line SLi, but also the resistance and capacitance of the signal line DLi are increased. Therefore, the time taken for the signal charge on the signal line DLi to move to the signal readout circuit 13 becomes longer. It is thus necessary to provide a longer time between the transition of the voltage of the scanning line SLj and sampling. As a result, the time taken for one scanning becomes longer, and it is difficult to read out the signals in real-time like the fourth embodiment.

However, like the fifth embodiment, when the signal lines DLi are divided into two parts, i.e., upper and lower regions, the time constant of the signal line DLi becomes substantially ¼ because of the same principle as that explained in the fourth embodiment. Thus, there is no need to provide a particularly long time between the transition of the voltage of the scanning line SLj and the sampling of the signals. Hence, even when the size of the X-ray detector 2 is increased and the number of pixels is also increased, like the first embodiment, it is possible to achieve high-speed signal readout with low noise by performing interlaced scanning in the fluoroscopy mode. In addition, even when the X-ray detector 2 is further increased in its size and precision, high-speed signal readout can be achieved by combining the fifth embodiment and the fourth embodiment.

Furthermore, like the fifth embodiment, when the scanning line drive circuits 12a and 12b are provided in association of the divided regions 41 and 42, respectively, it is possible to scan the scanning lines independently in each of the divided regions 41 and 42. Therefore, the scanning time of one screen is reduced to a half of the time taken for scanning all the scanning lines with a single scanning line drive circuit. Consequently, compared with the structure using a single scanning line drive circuit, it is possible to perform signal readout and display at higher speeds.

[Sixth Embodiment]

The following description will explain other embodiment of the present invention. For the sake of convenience of explanation, the structures having the same functions as those in the first to fifth embodiments will be designated by the same codes and the explanation thereof will be omitted.

With conventional TV signals of the NTSC (National Television System Committee) method or the like, in order to limit flickering during display and diminish the transmission band, jumping of a scanning line is performed. In resent years, with an improvement of the LSI technique, various techniques for achieving high image quality by digital image processing have been developed, and employed in a TV receiver. It is also possible to apply such a technique for achieving high image quality to image signals read out by interlaced scanning which is a characteristic of the present invention.

Typical techniques for achieving high image quality include progressive scanning display which displays an image by conversion from the interlaced scanning method to the sequential scanning method, and format conversion which matches the input image signals to the resolution of the display device. As the former technique, a method of forming a frame image by alternately interpolating an odd-number field and an even-numbered field using a frame memory and performing the progressive scanning display at twice the speed is most convenient.

As the technique for achieving high image quality, there is also movement adaptable scanning line interpolation processing. This processing detects a movement of an image in each small region of the screen to discriminate whether the image is a still image or an actively moving image, and switches the ways of generating interpolation signals. In a still image section, interpolation is performed using signals in one field before. On the other hand, in a moving image section, interpolation is performed using signals of upper and lower adjacent scanning lines in the current field. Consequently, it is possible to provide an image display with less deterioration of the image quality in the moving image section. Besides, in the still image section, like the above, interpolation may be performed using the signals in one field before and the signals of upper and lower scanning lines in the current field.

Meanwhile, it is also possible to reduce the noise in the still image section by performing the addition of images in a time axis direction which is used in an industrial-use image processing device having much noise. More specifically, in this case, weighted addition of the image signals of the previous frame and the image signals of the current frame may be performed.

The image processing techniques described here are known established techniques, and can be easily applied to the image processing device 5 shown in FIG. 2. Therefore, even when a readout operation mode using interlaced scanning is performed in the X-ray imaging apparatus of the present invention, it is possible to provide a high image quality display with less deterioration of the image quality.

In the above, various embodiments are explained by illustrating a direct conversion type X-ray imaging apparatus as an example. However, considering the scope of the present invention, the present invention is not necessarily limited to these embodiments and is, of course, applicable to an indirect conversion type X-ray imaging apparatus. Moreover, it is, of course, possible to combine the above-described embodiments with each other.

Further, interlaced scanning of TV signals is performed for the purpose of diminishing the transmission band, and is thus based on a different concept from interlaced scanning of the present invention which is designed for the purpose of improving two-line simultaneous scanning. Accordingly, the present invention is not derived from the interlaced scanning of TV signals.

As described above, an X-ray imaging apparatus according to the present invention includes X-ray irradiating means for irradiating X-rays on a specimen, two-dimensionally arranged X-ray detecting elements for converting the X-rays passed through the specimen into charge and storing the charge, switching elements provided in association with the X-ray detecting elements, respectively, a scanning line drive circuit for driving the switching elements through scanning lines row by row, and a signal readout circuit for reading out, column by column, charge signals output from the X-ray detecting elements to signal lines through the switching elements and outputting the charge signals as image signals, and may be configured so that the scanning line drive circuit switches scanning between sequential scanning of the scanning lines and interlaced scanning which scans at least every other scanning line, according to an imaging mode of the specimen, to drive the switching elements.

Moreover, the X-ray imaging apparatus of the present invention may be configured so that the X-ray irradiating means irradiates X-rays continuously on the specimen during interlaced scanning of the scanning lines.

For example, when performing pulse irradiation of X-rays on the specimen during interlaced scanning of the scanning lines, it is necessary to arrange a timing of pulse irradiation and a scanning timing for signal readout not to overlap each other so as to avoid such an event that the irradiation time of X-rays varies depending on the positions of the scanning lines. In this case, the cycle of one frame becomes longer by an amount corresponding to the difference between these timings.

However, when performing continuous X-ray irradiation on the specimen, the irradiation time of X-rays is uniform irrespective of the positions of the scanning lines and hence the above-mentioned arrangement is not necessary. Thus, the above-mentioned configuration can shorten the cycle of one frame compared with the pulse irradiation of X-rays.

Furthermore, the X-ray imaging apparatus of the present invention may be configured so that the signal readout circuit includes an integrating circuit of input charge signals.

With this configuration, even when a signal readout by the signal readout circuit is very small, it can be detected with high sensitivity.

Additionally, the X-ray imaging apparatus of the present invention may be configured so that the signal readout circuit includes an amplification factor switching circuit for switching the amplification factor of the input signal from the integrating circuit, according to the imaging mode.

It has been known that there is a two-digit-scale difference in the quantity of X-rays per frame between the radiography mode and the fluoroscopy mode. Hence, there is also an around two-digit-scale difference in the quantity of the resultant signals. Thus, like the above configuration, by providing the amplification factor switching circuit to change the amplification factor of the input signal according to the imaging mode, processing to be performed in stages later than the amplification factor switching circuit can be executed accurately according to the imaging mode.

In addition, the X-ray imaging apparatus of the present invention may be configured so that the signal readout circuit includes an adder circuit for adding input signals through a plurality of signal lines.

When correlated input signals (voltages) are added, the input signals are substantially doubled and hence the quantity of the signals is certainly increased compared with that obtained by addition of non-correlated input signals. Thus, according to this configuration, the signal-to-noise ratio can be improved by providing the adder circuit.

Besides, the X-ray imaging apparatus of the present invention may be configured so that the scanning line drive circuit is provided on both ends of the scanning lines.

With this configuration, it can be considered that each scanning line is substantially divided at the center thereof, and driven from both ends of the scanning line. In this case, since the resistance and capacitance of the scanning line become ½ of those before division, the time constant expressed by the product of the resistance and capacitance is substantially ¼ of the value before division. It is thus possible to significantly limit the rounding of the drive waveform on the scanning line and perform uniform signal readout. As a result, even when the number of X-ray detecting elements (the number of pixels) is increased, high-speed signal readout can be achieved with low noise.

In the X-ray imaging apparatus of the present invention, each signal line may be divided at the substantially center thereof, and the divided signal lines may be respectively connected to the signal readout circuits.

With this configuration, the resistance and capacitance of the divided signal line become ½ of those before division, and the time constant expressed by the product of the resistance and capacitance is substantially ¼ of the value before division. As a result, the time taken for the charge signal on the signal line to move to the signal readout circuit is shortened, and the time between the transition of the voltage of the scanning line and sampling of the signal is also shorten. Therefore, even when the number of X-ray detecting elements (the number of pixels) is increased, high-speed signal readout can be achieved with low noise. This effect can be further enhanced if this configuration is combined with the configuration of providing the scanning line drive circuit on both ends of the scanning lines.

Moreover, the X-ray imaging apparatus of the present invention may further include an image processing apparatus for performing movement adaptable scanning line interpolation with respect to the signals read out by the interlaced scanning.

With this configuration, it is possible to obtain an image with less deterioration of image quality in a moving image section by the movement adaptable scanning line interpolation performed in the image processing apparatus.

Furthermore, the X-ray imaging apparatus of the present invention may further include an image processing apparatus for updating a frame image by performing weighted addition of the current frame image and previous frame image obtained based on the signals read out by the interlaced scanning.

With this configuration, since the image processing device performs the weighed addition of the frame images in a time axis direction, it is possible to reduce noise in a still image section.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An X-ray imaging apparatus comprising:
   X-ray irradiating means for irradiating X-rays on a specimen;
   X-ray detecting elements, arranged two-dimensionally, for converting X-rays obtained through the specimen into charge and storing the charge;
   switching elements provided in association with said X-ray detecting elements, respectively; and
   a scanning line drive circuit for driving said switching elements row by row through scanning lines,
   wherein said scanning line drive circuit drives said switching elements by selectively performing sequential scanning of the scanning lines or interlaced scanning which scans at least every other scanning line, according to an imaging mode of the specimen.

2. The X-ray imaging apparatus as set forth in claim 1, wherein said scanning line drive circuit performs sequential scanning of the scanning lines in a first imaging mode for imaging a static specimen, while performs interlaced scanning of the scanning lines in a second imaging mode for imaging a dynamic specimen.

3. The X-ray imaging apparatus as set forth in claim 1, wherein, when performing interlaced scanning of scanning every (p+1)th scanning lines, p being an integer of not less than 1, said scanning line drive circuit performs the interlaced scanning according to a timing given by a clock signal which is a pulse signal produced at unequal intervals for generating a scanning timing of the scanning line and a signal which is generated at intervals of (p+1) pulses of the clock signal for making an output from said scanning line drive circuit effective.

4. The X-ray imaging apparatus as set forth in claim 1, wherein, when performing interlaced scanning of the scanning lines, said scanning line drive circuit scans the scanning lines at intervals of a plurality of scanning lines.

5. The X-ray imaging apparatus as set forth in claim 1, wherein, when performing interlaced scanning of the scanning lines, said X-ray irradiating means irradiates X-rays continuously on the specimen.

6. The X-ray imaging apparatus as set forth in claim 1, wherein, when performing interlaced scanning of the scanning lines, said X-ray irradiating means performs pulse irradiation of X-rays on the specimen at a timing that does not overlap a scanning timing of each scanning line.

7. The X-ray imaging apparatus as set forth in claim 1, further comprising a signal readout circuit for reading out, column by column, charge signals output from said X-ray detecting elements to signal lines through said switching elements and outputting the charge signals as image signals, said signal readout circuit including an integrating circuit for storing and converting charge of input charge signals into a voltage.

8. The X-ray imaging apparatus as set forth in claim 7, wherein said signal readout circuit further includes an amplification factor switching circuit for switching an amplification factor of an input signal from said integrating circuit, according to the imaging mode.

9. The X-ray imaging apparatus as set forth in claim 1, further comprising a signal readout circuit for reading out, column by column, charge signals output from said X-ray detecting elements to signal lines through said switching elements, and outputting the charge signals as image signals, said signal readout circuit including an adder circuit for adding the input signals through a plurality of signal lines.

10. The X-ray imaging apparatus as set forth in claim 1, wherein said scanning line drive circuit is composed of a first scanning line drive circuit and a second scanning line drive circuit which are provided on both ends of the scanning lines, respectively.

11. The X-ray imaging apparatus as set forth in claim 1, further comprising a signal readout circuit for reading out, column by column, charge signals output from said X-ray detecting elements to signal lines through said switching elements, and outputting the charge signals as image signals, wherein each of the signal lines is divided, and said signal readout circuit is composed of a plurality of sub signal readout circuits provided in association with the divided signal lines, respectively.

12. The X-ray imaging apparatus as set forth in claim 11, wherein said scanning line drive circuit is composed of a plurality of sub scanning line drive circuits provided in association with said sub signal readout circuits, respectively.

13. The X-ray imaging apparatus as set forth in claim 11, wherein each signal line is divided into two parts at a substantially center thereof.

14. The X-ray imaging apparatus as set forth in claim 1, further comprising an image processing device for performing movement adaptable scanning interpolation with respect to signals read out by the interlaced scanning.

15. The X-ray imaging apparatus as set forth in claim 1, further comprising an image processing device for updating a frame image by performing a weighted addition of a current frame image and a previous image obtained based on signals read out by the interlaced scanning.

16. An X-ray imaging apparatus comprising:

X-ray irradiating means for irradiating X-rays on a specimen;

X-ray detecting elements, arranged two-dimensionally, for converting X-rays obtained through the specimen into charge and storing the charge;

switching elements provided in association with said X-ray detecting elements, respectively; and a scanning line drive circuit for driving said switching elements row by row through scanning lines, wherein said scanning line drive circuit performs scanning of the scanning lines according to individual imaging modes so that a variation of charge of signal lines during a transition of a scanning line voltage does not differ between different imaging modes of the specimen.

17. An X-ray detecting device for detecting X-rays irradiated on a specimen, comprising:

X-ray detecting elements, arranged two-dimensionally, for converting X-rays obtained through the specimen into charge and storing the charge;

switching elements provided in association with said X-ray detecting elements, respectively; and a scanning line drive circuit for driving said switching elements row by row through scanning lines, wherein said scanning line drive circuit drives said switching elements by selectively performing sequential scanning of the scanning lines or interlaced scanning which scans at least every other scanning line, according to an imaging mode of the specimen.

\* \* \* \* \*